(12) United States Patent
Carabe-Fernandez et al.

(10) Patent No.: US 11,794,038 B2
(45) Date of Patent: Oct. 24, 2023

(54) PROTON BEAM SYSTEM AND METHODS FOR IRRADIATING A TARGET

(71) Applicant: THE TRUSTEES OF THE UNIVERSITY OF PENNSYLVANIA, Philadelphia, PA (US)

(72) Inventors: Alejandro Carabe-Fernandez, Philadelphia, PA (US); Peter Kimstrand, Stockholm (SE)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 303 days.

(21) Appl. No.: 16/969,999

(22) PCT Filed: Feb. 19, 2019

(86) PCT No.: PCT/US2019/018560
§ 371 (c)(1),
(2) Date: Aug. 14, 2020

(87) PCT Pub. No.: WO2019/164835
PCT Pub. Date: Aug. 29, 2019

(65) Prior Publication Data
US 2021/0101027 A1 Apr. 8, 2021

Related U.S. Application Data

(60) Provisional application No. 62/632,579, filed on Feb. 20, 2018.

(51) Int. Cl.
*A61N 5/10* (2006.01)
(52) U.S. Cl.
CPC .......... *A61N 5/1081* (2013.01); *A61N 5/103* (2013.01); *A61N 5/1031* (2013.01); *A61N 5/1043* (2013.01); *A61N 2005/1087* (2013.01)

(58) Field of Classification Search
None
See application file for complete search history.

(56) References Cited

U.S. PATENT DOCUMENTS 8,139,060 B2 3/2012 Brown et al.
9,155,912 B2 * 10/2015 Yu .................. A61B 6/4452
(Continued)

OTHER PUBLICATIONS

Carabe-Fernandez et al., "SU-E-T-640: Proton Modulated Arc Therapy Using Scanned Pencil Beams," Med. Phys., vol. 42, 2015, pp. 3483-3483.

(Continued)

*Primary Examiner* — Hoon K Song
(74) *Attorney, Agent, or Firm* — BakerHostetler

(57) ABSTRACT

A method for creating an irradiation plan. The method may include receiving an irradiation therapy plan for irradiating a target with a proton beam from a gantry. The irradiation therapy plan may have a plurality of irradiation spots for delivering protons to the target. The method may include identifying a rotational profile for angular rotation of the gantry with respect to the target, a slew time for a proton beam to travel between each of the plurality of irradiation spots, and an amount of protons to be delivered to each irradiation spot. The method may also include creating an irradiation plan. The irradiation plan may include a plurality of groups of irradiation spots based on the rotational profile, the slew time, and the amount of protons to be delivered to each irradiation spot. Each group of irradiation spots may be associated with a respective portion of the angular rotation.

23 Claims, 20 Drawing Sheets

(56) References Cited

U.S. PATENT DOCUMENTS

| | | | |
|---|---|---|---|
| 9,241,212 B2 | 1/2016 | Hur et al. | |
| 9,289,627 B2* | 3/2016 | Otto | G01T 1/29 |
| 2017/0157426 A1 | 6/2017 | Buchsbaum | |
| 2017/0285122 A1* | 10/2017 | Kaditz | G01R 33/445 |

OTHER PUBLICATIONS

Ding et al., "Spot-Scanning Proton Arc (SPArc) Therapy: The First Robust and Delivery-Efficient Spot-Scanning Proton Arc Therapy," Int. J. Radiat. Oncol. Biol. Phys., vol. 96, 2016, pp. 1107-1116.

Grassberger et al., "Variations in Linear Energy Transfer Within Clinical Proton Therapy Fields and the Potential for Biological Treatment Planning," Int. J. Radiat. Oncol., vol. 80, 2011, pp. 1559-1566.

Kataria et al., "Homogeneity Index: An objective tool for assessment of conformal radiation treatments," J. Med. Phys., vol. 37, 2012, pp. 207-213.

Low et al., "A technique for the quantitative evaluation of dose distributions," Med. Phys., vol. 25, 1998, pp. 656-661.

Mizumoto et al., "Proton Beam Therapy for Pediatric Brain Tumor Neurol," Med. Chir. (Tokyo)., vol. 57, 2017, pp. 343-355.

Peeler et al., "Clinical evidence of variable proton biological effectiveness in pediatric patients treated for ependymoma Radiother," Oncol., vol. 121, 2016, pp. 395-401.

Pulliam et al., "Comparison of 2D and 3D gamma analysis", Medical Physics, vol. 41, No. 2, Feb. 2014, Retrieved on Apr. 8, 2019 from internet https://www.ncbi.nlm.nih.gov/pmc/articles/PMC3977814/pdf/MPHYA6-000041-021710_1.pdf.

Rah et al., "A treatment planning study of proton arc therapy for para-aortic lymph node tumors: dosimetric evaluation of conventional proton therapy, proton arc therapy, and intensity modulated radiotherapy," Radiat. Oncol., vol. 11, 2016, pp. 140, 10 pages.

Rechner et al., "Risk of radiogenic second cancers following volumetric modulated arc therapy and proton arc therapy for prostate cancer," Phys Med. Biol., vol. 57, 2012, pp. 7117-7132.

Riet et al., "A conformation number to quantify the degree of conformality in brachytherapy and external beam irradiation: Application to the prostate," Int. J. Radiat. Oncol. Biol. Phys., vol. 37, 2017, pp. 731-736.

Sanchez-Parcerisa et al., "Range optimization for mono- and bi-energetic proton modulated arc therapy with pencil beam scanning," Phys. Med. Biol., vol. 61, 2016, pp. N565-N574.

Sandison et al., "Phantom assessment of lung dose from proton arc therapy," Int. J. Radiat. Oncol. Biol. Phys., vol. 38, 1997, pp. 891-897.

Seco et al., "Proton arc reduces range uncertainty effects and improves conformality compared with photon volumetric modulated arc therapy in stereotactic body radiation therapy for non-small cell lung cancer," Int. J. Radiat. Oncol. Biol. Phys., vol. 87, 2013, pp. 188-194.

Unkelbach et al., "Reoptimization of intensity-modulated proton therapy plans based on linear energy transfer," Int. J. Radiat. Oncol. Biol. Phys., vol. 96, 2016, pp. 1097-1106.

Wieser et al., "Development of the open-source dose calculation and optimization toolkit matRad," Med. Phys., vol. 44, 2017, pp. 2556-2568.

Wilkens et al., "Three-dimensional LET calculations for treatment planning of proton therapy," Z. Med. Phys., vol. 14, 2004, pp. 41-46.

Wouters et al., "Radiobiological intercomparison of the 160 MeV and 230 MeV proton therapy beams at the Harvard Cyclotron Laboratory and at Massachusetts General Hospital," Radiat Res., vol. 183, 2015, pp. 174-187.

\* cited by examiner

Static irradiation plan

Irradiation plan having groups of irradiation spots

PROTON BEAM SYSTEM AND METHODS FOR IRRADIATING A TARGET

CROSS-REFERENCE TO RELATED APPLICATIONS

This application is the National Stage Application of International Patent Application No. PCT/US2019/018560, filed Feb. 19, 2019, which claims the benefit of and priority to U.S. Provisional Application No. 62/632,579, filed Feb. 20, 2018, the entireties of which applications are is hereby incorporated by reference in its their entireties for any and all purposes.

FIELD OF THE INVENTION

This disclosure relates to systems and method for creating an irradiation plan and for irradiating a target.

BACKGROUND OF THE INVENTION

Charged particle therapy systems have proven applications in the treatment of cancerous cells. Conventional radiation therapy uses X-rays which pass through the target volume and deliver an undesirable exit dose to healthy tissue. A charged particle beam path can be terminated at a precise location, minimizing damage to healthy tissue surrounding the target volume.

Conventional methods of delivering charged particles in pencil beam scanning (PBS) mode require the target volume be treated in layers, with each layer corresponding to a different charged particle beam energy level. Inter-layer switching time, which includes changing the energy level of the charged particle beam, can vary between several microseconds to several seconds and undesirably leads to extended treatment times. For example, if the dose was to be delivered while the particle gantry or patient positioning device (PPS) rotates, the radiation dose cannot be delivered fast enough to all the layers at a given gantry or PPS angle. Thus, there is a need for more sophisticated particle therapy systems.

SUMMARY OF THE INVENTION

Methods and systems are disclosed for providing a therapy. An example method may include receiving an irradiation therapy plan for irradiating a target with a proton beam from a gantry. The irradiation therapy plan may include a plurality of irradiation spots for delivering protons to the target. The method may include identifying a rotational profile for angular rotation of the gantry with respect to the target, a slew time for a proton beam to travel between each of the plurality of irradiation spots, and an amount of protons to be delivered to each irradiation spot. Additionally, the method may include creating an irradiation plan. The irradiation plan may include a plurality of groups of irradiation spots based on the rotational profile, the slew time, and the amount of protons to be delivered to each irradiation spot. Each group of irradiation spots may be associated with a respective portion of the angular rotation.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. For the purposes of illustration, there are shown in the drawings example embodiments of various aspects of the disclosure; however, the invention is not limited to the specific methods and instrumentalities disclosed.

DETAILED DESCRIPTION OF THE INVENTION

Figure 1:
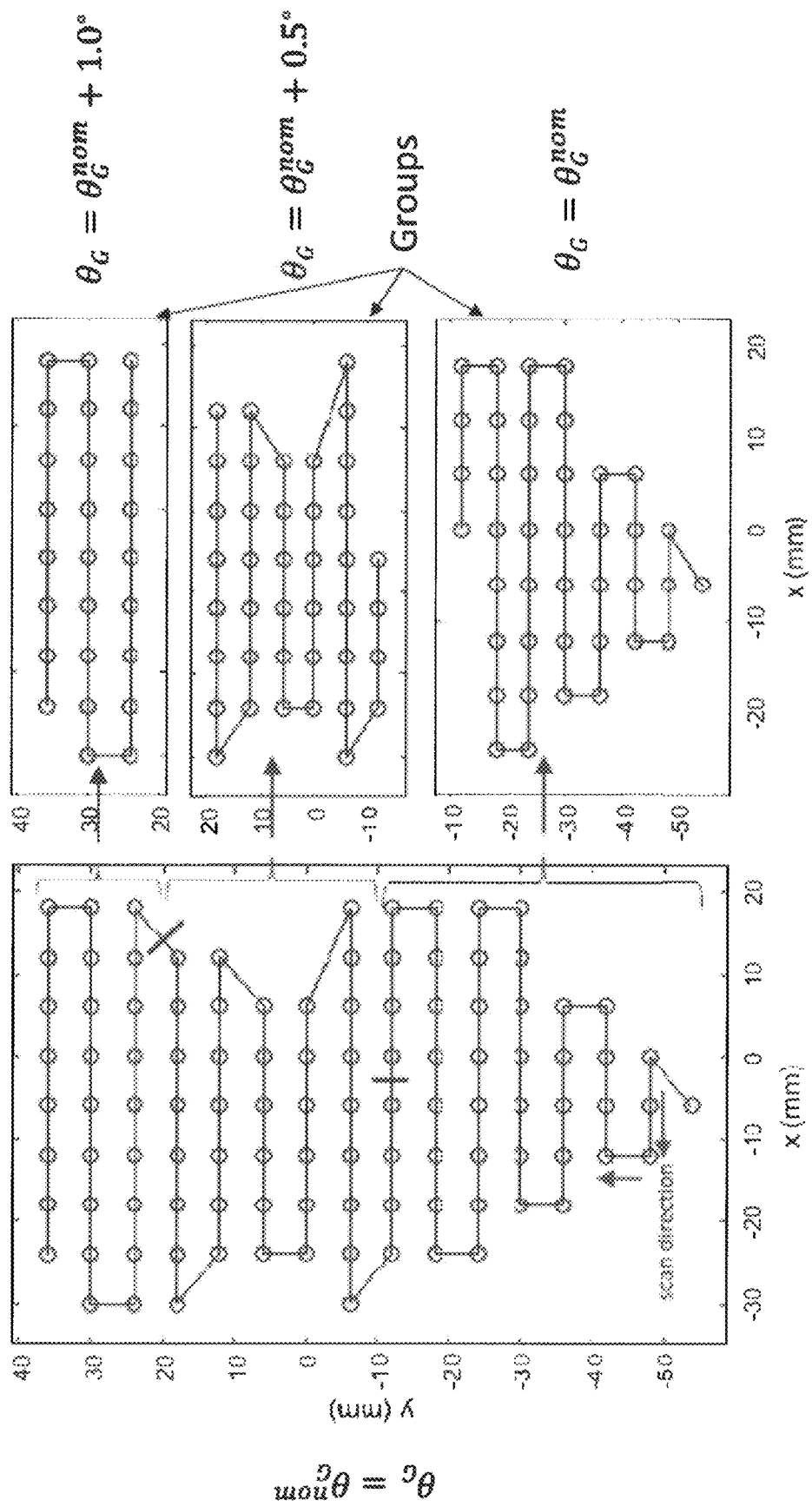
FIG. 1 illustrates an irradiation therapy plan and an irradiation plan having three groups of irradiation spots according to aspects of the invention.

Disclosed are systems and methods for irradiating a planning target with protons and proton beam therapy systems. The following descriptions are meant to provide example embodiments of the present invention. The scope of the claims is not intended to be limited by any of the particular embodiments disclosed below.

Proton therapy has benefits over than photon beam therapy due to the properties of the proton dose distribution, which provides no exit dose and the ability to achieve similar conformity while using fewer proton beams. Proton beams may be delivered as static beams, where each beam is constructed by either passive scattering or by active scanning. In the case of scanned proton beams, the individual spot weights (i.e., the proton dosage at a particular irradiation spot) may be optimized to either achieve a uniform proton dose for the target (hereafter "SFUD") or to produce a proton dosage plan without any restrictions on proton beam dose homogeneity (hereafter "IMPT").

These different delivery methodologies are based on the fact that proton therapy offers physical properties that allow dose optimization beyond conventional radiotherapy. In addition, proton beams have the following benefits over conventional radiotherapy treatment: (1) protons have higher linear energy transfer (hereafter "LET") at the distal edge of the Bragg peak, where they also present a higher biological effectiveness; and (2) there is a tendency to distribute the weight of the proton dose in an increasing number of fields, to reduce the possible impact of biological enhancement at the distal edge of the Bragg peak. For instance, in the case of brain treatments, it is usual to use three orthogonal fields of equal weight and with very little overlap of the distal edges of the beams. This enables the reduction of the dose at the entrance channel of each beam and helps avoid hot spots of LET in the normal tissue surrounding the target volume. The truly advantageous situation would be to have the higher LET components inside the target volume rather than in the normal tissue immediately outside the target. One answer to this problem is to deliver the proton beam in an arc, optimizing the range of the protons to have a single Bragg peak in the mid plane of the target volume.

The present disclosure improves over conventional approaches at least by recognizing that a continuously rotating gantry would provide improvement over methods that repeatedly stop and start the gantry during a treatment plan employing proton beams. For example, starting and stopping the gantry rotation every few degrees will both increase the time for delivering the dosage according to the treatment and create stress, and potential breakage, in the gantry's supporting structure. Importantly, the continuous rotation of the gantry while delivering a proton beam causes interplay effects between the movements of the system.

As used herein, an irradiation therapy plan refers to the predetermined plan for delivering a desired proton dosage to a target based on the delivery of protons to identified locations of the target. The irradiation therapy plan may be created by any suitable process known by one of ordinary skill in the art.

An irradiation plan, as used herein, is the plan for delivering the desired proton dosage/amount to each irradiation spot using a gantry that continuous rotates with respect to the target. The irradiation plan may account for the delivery of protons to one or more irradiation spots at different portions of the gantry's angular rotation, while the irradiation therapy plan often does not account for the protons to be delivered to each irradiation spot at different portions of the angular rotation of the gantry. For example, FIG. 1 illustrates an irradiation therapy plan on the left and an irradiation plan on the right having three groups of irradiation spots.

Figure 2:
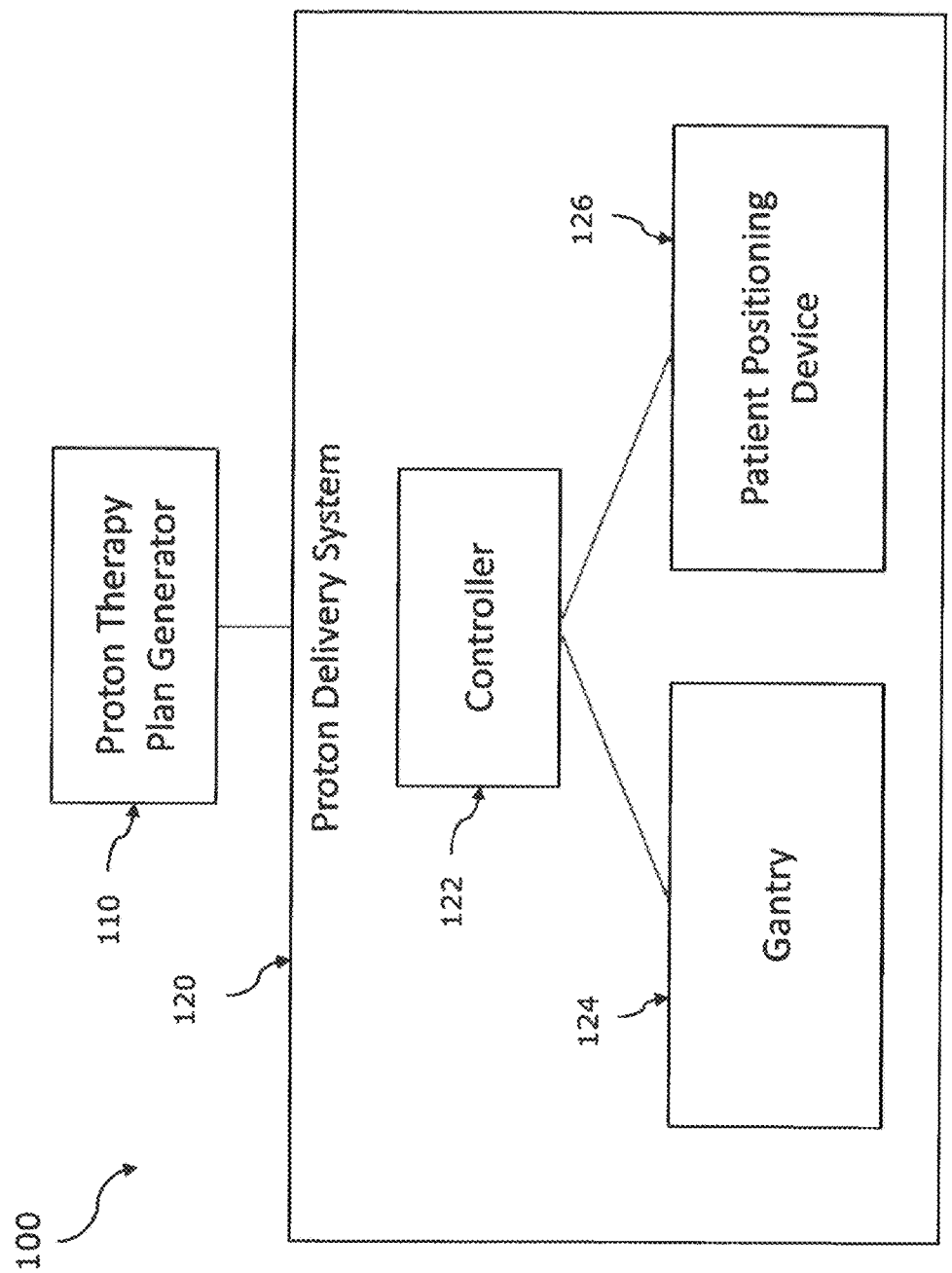
FIG. 2 is a schematic of a system for delivering protons from a gantry to a target in accordance with aspects of the invention.

FIG. 2 illustrates a system 100 for delivering protons from a gantry to a target while the gantry rotates with respect to the target. As a general overview, system 100 includes a proton therapy plan generator 110 and a proton delivery system 120.

Proton therapy plan generator 110 may be any device or apparatus suitable for generating an irradiation therapy plan. For example, proton therapy generator 110 may include at least one processor, controller, memory chip, computer, and/or the like.

Proton delivery system 120 may be used for delivering at least one proton beam to one or more irradiation spots of the target in accordance with an irradiation plan, which is further discussed below. Proton delivery system 120 may include one or more of a controller 122, a gantry 124, or a patient positioning system 126. Proton delivery system 120 may deliver a proton beam having a beam current of about 0.01 nÅ to about 30 nÅ or, e.g., about 0.1 nÅ to about 20 nÅ, about 1 nÅ to about 10 nÅ, or about 2 nÅ to about 6 nÅ. In one embodiment, proton delivery system 120 delivers a proton beam having a beam current of about 4 nÅ.

Gantry 124 may include an apparatus for delivering a desired proton dosage (e.g., an amount of protons) to the target. Gantry 124 may rotate with respect to the target during the delivery of the protons to the target, e.g., to a plurality of positions in an arc around target. An arc may include at least a portion of 360 degrees about the target. The rotation may be centered on the planning target, or it may be centered elsewhere. In one embodiment, the gantry rotates continuously, but delivers charged particles to less than all positions within the arc (e.g., it does not deliver charged particles to the entire arc). Gantry 124 may rotate continuously at a consistent speed or at a variable speed during the delivery of protons to the target. For example, gantry 124 may rotate continuously with respect to patient positioning system 126 at a consistent speed of 0-1 rpm, 1-2 rpms, 2-3 rpms, 3-4 rpms, or more. In one embodiment, gantry 124 rotates continuously with respect to patient positioning system 126 at a consistent speed of 1 rpm. Alternatively, the speed of rotation for gantry 124 may vary during the delivery of protons to the target.

Gantry 124 may be configured to transport and deliver a charged particle beam into a treatment room, bend a proton beam until it is incident and/or orthogonal to the target, and rotate a beam around the target. The gantry may be comprised of large magnets, an evacuated pipe, a nozzle, and a counterweight. All of the components may be mounted on a large steel beam or a "squirrel cage" to enable the rotation of the proton beam around the target.

Patient positioning system 126 is configured to support a patient thereon. Patient positioning system 126 may be used to rotate the patient to a plurality of positions with respect to a positionally fixed gantry, such that gantry 124 rotates with respect to the target.

Patient positioning system 126 may rotate continuously at a consistent speed or a variable speed during the delivery of the protons to the target. For example, patient positioning system 126 may rotate continuously with respect to gantry 124 at a consistent speed of 0-1 rpm, 1-2 rpms, 2-3 rpms, 3-4 rpms, or more. In one embodiment, patient positioning system 126 rotates continuously with respect to gantry 124 at a consistent speed of 1 rpm. Alternatively, the speed of rotation for patient positioning system 126 may vary during the delivery of protons to the target.

Figure 3:
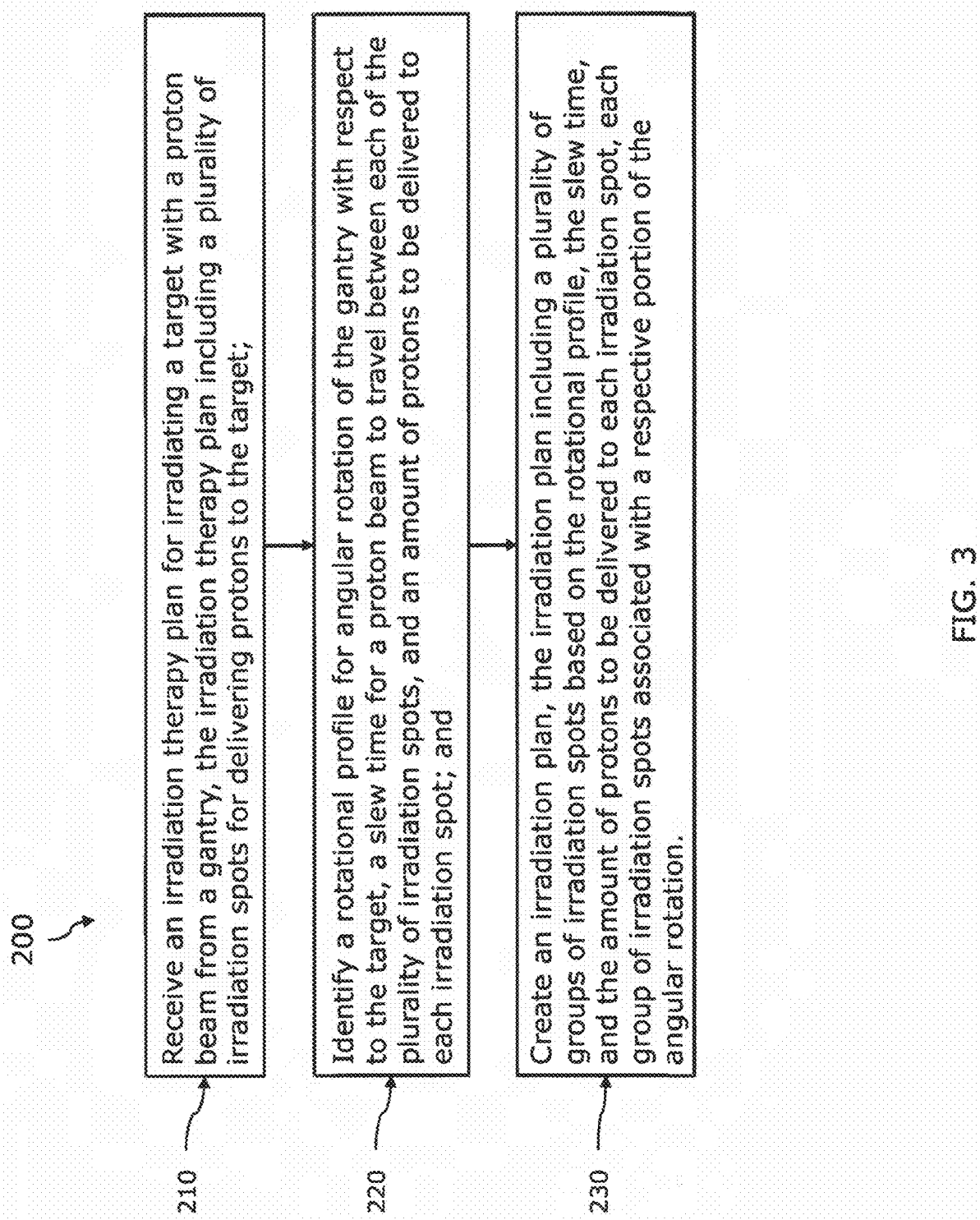
FIG. 3 is a schematic of a method for creating an irradiation plan in accordance with an aspect of the invention.

FIG. 3 is a flow chart of a method 200 for creating an irradiation plan in accordance with an aspect of the invention. As a general overview, method 200 may including one or more of: receiving an irradiation therapy plan in step 210; identifying a rotational profile, a slew time, and an amount of protons for delivery in step 220; or creating an irradiation plan in step 230.

In step 210, an irradiation therapy plan may be received (e.g., from another computing device, from input by a user) for irradiating a target with a proton beam from a gantry. The irradiation therapy plan may include a plurality of irradiation spots for delivering protons to a target. A spot map for delivering a desired proton dosage to a target by delivering desired proton dosages to one or more of the irradiation spots may be produced using Raytracing. Suitable raytracing algorithms and/or programs are further described in U.S. Pat. Nos. 8,139,060 and 9,241,212, which are incorporated herein in their entirety for all purposes.

In step 220, one or more parameters may be determined (e.g., or identified, calculated). The plurality of parameters may be associated with controlling a gantry, associated with irradiation, and/or the like. The plurality of parameters may include a rotational profile for the angular rotation of the gantry with respect to the target, a slew time for a proton beam to travel between each of the plurality of irradiation spots, an amount of protons to be delivered to each irradiation spot, and/or a combination thereof. The rotational profile for the angular rotation of the gantry may be based on a consistent speed of rotation or a variable speed of rotation of the gantry with respect to the target. For example, the gantry may be continuously rotated with respect to the target at a consistent speed of rotation of 0-1 rpm, 1-2 rpms, 2-3 rpms, 3-4 rpms, or more. In one embodiment, the gantry rotates continuously with respect to the target at a consistent speed of 1 rpm. Alternatively, the speed of rotation for the gantry with respect to the target may vary during the delivery of protons to the target. As discussed above, the target may be rotated using a patient positioning device while the gantry remains in the same location, such that the gantry rotates with respect to the target.

Figure 4:
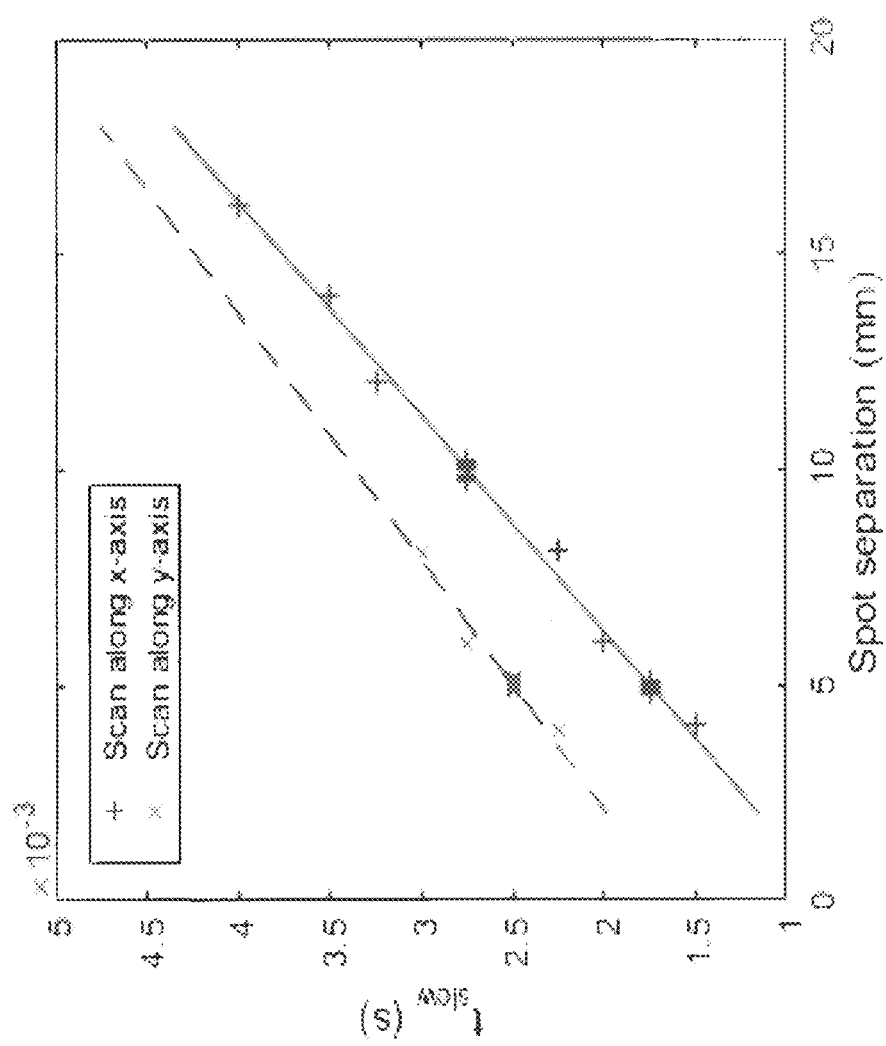
FIG. 4 is a graph of the slew time as a function of the spot distance in accordance with aspects of the present invention.

The slew time can be determined as a function of the distance between irradiation spots and the speed at which the proton beam is manipulated between such irradiation spots. For example, data may be extracted from beam delivery log files to determine a slew time between each neighboring irradiation spots, thereby creating the slew time as a function of the distance between irradiation spots (See, e.g., FIG. 4).

The data may be fitted to a linear function and the slew time for a given spot separation ($\Delta x$, $\Delta y$) may be calculated as:

$$t_{slew}(\Delta x, \Delta y) = max(t_{slew}(\Delta x), t_{slew}(\Delta y))$$

Figure 5:
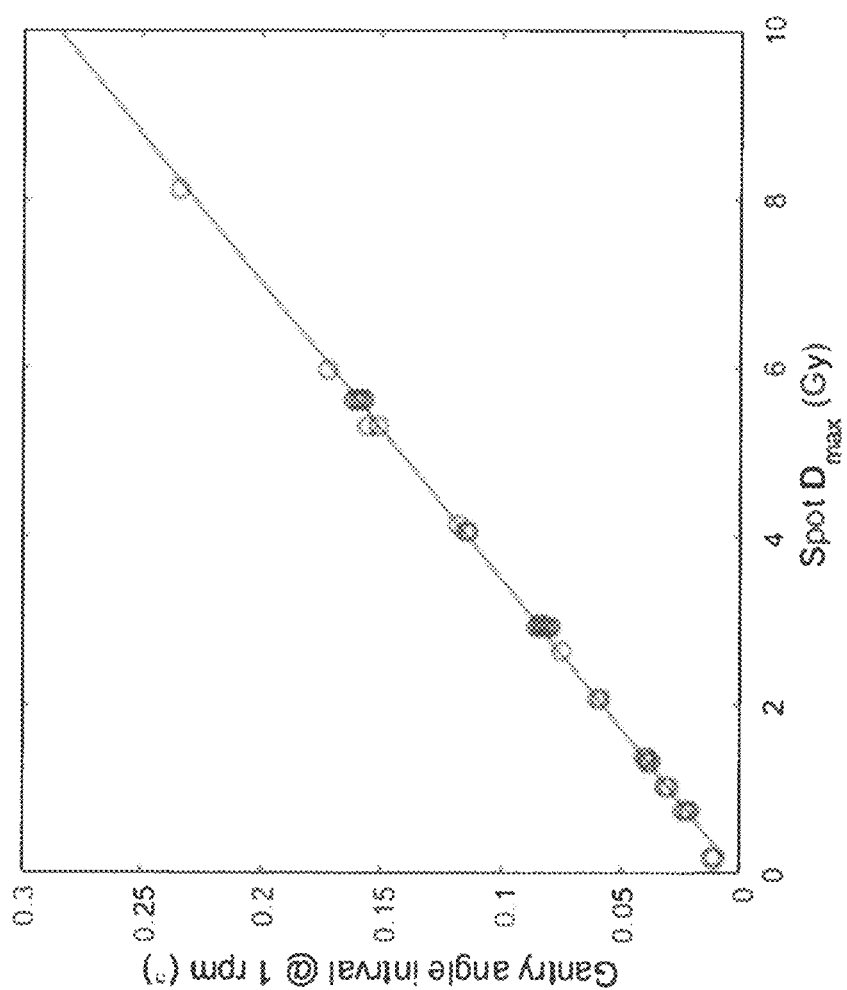
FIG. 5 is a graph of the gantry angle interval at a gantry rotation speed of 1 rpm compared to Dmax of one spot at E=175 MeV according to aspects of the present invention.

The amount of time required to deliver an irradiation spot as a function of the proton dosage it deposits may also be determined based on the beam delivery log files. A deposited proton dose (e.g., the deposited amount of protons) may be preferred over Monitor Units (hereafter "MU") due to the lack of universal definition of MU in particle radiotherapy. The delivery time of the irradiation spot is dependent on the beam current, but the system may also have an overhead in the monitoring system (checking irradiation spot position etc.). Based on the data obtained from the beam delivery logs and the calculated proton dosage of the irradiation plan, a spot delivery time versus the planned maximum proton dose of the spot may be determined. Assuming a gantry rotation speed of 1 rpm, the fan angle traversed as a function of the maximum spot dose (e.g., as shown in FIG. 5) may be estimated.

The amount of protons to be delivered to each irradiation spot may be determined using known software programs and/or algorithms based on the original irradiation therapy plan. The beam current is dependent on the spot energy and, thus, the spot energy for this calculation may be chosen as the middle of the therapeutic range, E=175 MeV. In one embodiment, the spot time is derived using a beam current of 4 nA. The spot energy may be determined by the number of protons that need to be delivered at a given depth. The larger the depth, the larger the energy and the lower the beam current. The determination of the spot energy, therefore, depends on how far the protons need to travel though tissue. As shown in FIG. 5, even spots with a dose as high as 10 Gy can be delivered within 0.3 degree.

In step 230, an irradiation plan may be created (e.g., or generated, determined). The irradiation plan may include a plurality of groups of irradiation spots based on the rotational profile, a slew time, an amount of protons to be delivered to each irradiation spot, and/or a combination thereof. Each group of irradiation spots is associated with a respective portion of the angular rotation. For example, the proton dosage (e.g., the amount of protons) delivered at each irradiation spot within a group may be calculated based on the same angular rotation to increase the speed and efficiency of the calculations.

Equations 1 and 2, provided below, may be used to calculate a dose distribution that is applied to a target from a continuously rotating gantry. The slew time and beam current may be used to obtain the angular displacement of the gantry for each irradiation spot of the original spot map of the irradiation therapy plan, which may be based on the delivery of the protons to the irradiation spots using a static gantry (e.g., a gantry that is not continuously rotating while delivering the proton beams). The section of the arc described by each individual spot ($\Delta\theta_{G,i}$) is centered around the original static gantry angle, i.e., for a given control point i, with $n_i$ spots positioned at the nominal gantry angle $\Delta\theta_{G,nom,i}$ the gantry will in total rotate the angle interval.

$$\Delta\theta_{G,i} = \frac{d\theta_i}{dt}\left[\sum_{j=1}^{n_i} t_{slew,j} + t_{spot,j}\right] \quad (1)$$

Each spot j within the control point i may then be assigned its own gantry angle.

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

One or more groups of irradiation spots may be created. Each group of irradiation spots is associated with a portion of the angular rotation of the gantry (e.g., a gantry angle). Each group of irradiation spots, which are associated with a respective portion of the angular rotation, may be calculated using Equation (2). In, one embodiment, the irradiation plan is fully modelled to calculate a gantry angle for the delivery of protons to each irradiation spot, e.g., using a beam current of 4 nA. For example, the irradiation plan may calculate the proton dosage for each irradiation point at the angle of the gantry during the delivery of the protons to each respective irradiation spot. Creating groups of two or more irradiation spots may increase the expediency of determine the proton dosage amount for the irradiation plan because the dosage amount for each irradiation spot assigned to the group is calculated using the same respective portion of the angular rotation associated with the group. Thus, irradiation plans including a plurality of groups of two or more irradiation spots may be determined more quickly than an irradiation plan calculates the proton dosage for each irradiation point at the angle of the gantry during the delivery of the protons to each respective irradiation spot.

The number of groups of irradiation spots and the number of irradiation spots within each group effects the amount of time required for calculating the proton dosage delivered to each irradiation spot. For example, for a set number of irradiation spots, the amount of time required to calculate the proton dosage delivered to all of the irradiation spots decreases as the number of groups of irradiation spots decreases and the number of irradiation spots within each group of irradiation spots increases. Conversely, for a set number of irradiation spots, the amount of time required to calculate the proton dosage delivered to all of the irradiation spots increases as the number of groups of irradiation spots increases and the number of irradiation spots within each group of irradiation spots decreases.

The assignment of multiple irradiation spots to a group for calculation purposes effectively means that each group will take a longer time to be delivered as the group will encompass the cumulative spot time and the cumulative slew time for all the irradiation spots included in the group. The longer delivery time will in turn translate into a larger arc of spread of the dosage of protons to be delivered to that group of irradiation spots, and potentially leading to a decrease in the precision of the delivery of the irradiation therapy plan to the target.

In accordance with one aspect of the disclosure, method 200 may further include comparing the amount of protons to be delivered at the plurality of irradiation spots to a threshold value (e.g., to determine whether a suitable amount of the discharged protons would be delivered within the target and/or to the respective irradiation spot). The threshold value may be a value determined from gamma difference analysis. For example, the threshold value may be a gamma difference in dose of more than 10 mm/10%, more than 7 mm/ %, more than 5 mm/5%, more than 3 mm/3%, more than 2 mm/2% or more than 1 mm/1%. In one embodiment, if the threshold value is satisfied, then method 200 may reassign the irradiation spots to an increased number of groups of irradiation spots to increase the precision of the delivery of the proton dosage. Method 200 may perform iterative functions that assess the irradiation plan to optimize the number of groups of irradiation spots.

Additional description regarding the appropriateness of the number of groups of irradiation spots is provided below.

For treatment planning and dose calculation purposes, a scanned proton arc may comprise (e.g., or consist of) a number of irradiation plans, distributed over the full arc. Each irradiation plan may comprise a spot map of one or more spot positions and respective spot weights. All irradiation spots within the irradiation plan may be calculated at the same gantry angle and may have the same energy. The delivery of each irradiation plan is not instant, but rather may be dependent on: (i) the beam current, which determines the time it takes to deliver each spot; and (ii), the lateral scanning speed of the proton beam, which determines the time it takes to scan between the irradiation spots in the spot map of the irradiation therapy plan (referred to herein as the slew time).

This yields a non-negligible delivery time for each irradiation plan. Thus, an offset between the gantry angle and the planned spot map for each irradiation plan occurs as the gantry continuously rotates, unless the planned spot map for each irradiation plan is calculated to reflect the continuous rotation of the gantry. In order to eliminate this offset, the amount of irradiation dosage may be calculated for each irradiation spot of each irradiation plan at different gantry angles resulting from the gantry rotating, instead of calculating the amount of dosage for each irradiation spot at a single gantry angle according to a static irradiation plan (e.g., an irradiation plan where the gantry is not continuously rotating with respect to the target).

For a conventional static field (3D conformal) scanned proton beam, three factors add to the total beam delivery time: the switching of energies (referred to herein as the inter-layer time), the scanning in between irradiation spot positions (referred to herein as the slew time), and the actual spot delivery time (referred to herein as the spot time). For PMAT treatment plans, mono-energetic arcs may be used in accordance with U.S. patent application Ser. No. 15/328,135, which is incorporated herein in its entirety for all purposes. In accordance with U.S. patent application Ser. No. 15/328,135, the switching of energies may be performed a single time in between the delivery of the two arcs and, thus, the inter-layer time during each arc delivery may be eliminated for calculation purposes. Accordingly, the slew and spot times are the predominate factors for determining the total amount of time to deliver the proton dosage according to the treatment plan.

As an example of the effect of the slew time on the overall time for delivering the desired dosage of protons, a small cylindrical target with a cross section of 50×50 mm$^2$ and a spot separation of 6 mm may have a total slew time of 0.11 seconds and the angle interval traversed during the scan would be 0.64 degrees, if assuming a gantry rotation speed of 1 rotation per minutes ("rpm"). This is a small angle interval and the assumption of a static deliver for dose calculation (step and shoot dose distribution) could be considered a precise enough approximation to calculate PMAT dose distributions. However, if the cross section of the cylinder is 100×100 mm$^2$ with the same irradiation spot spacing and gantry rotation speed, the total slew time is 0.37 seconds and the interval traversed by the gantry increases to 2.24 degrees. The effect of this rotation during delivery is clearly not negligible and PMAT dose distributions cannot be calculated assuming static beams.

Figure 6A:
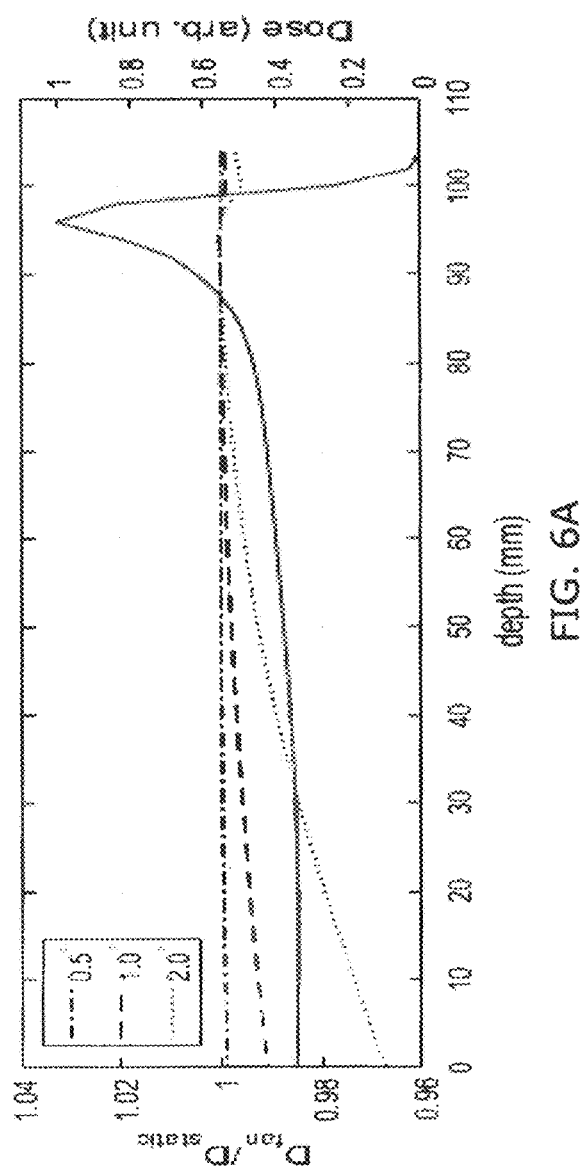
FIG. 6A is a graph of the depth dose along the central axis of an irradiation spot during continuous rotation of the gantry according to aspects of the invention.
Figure 6B:
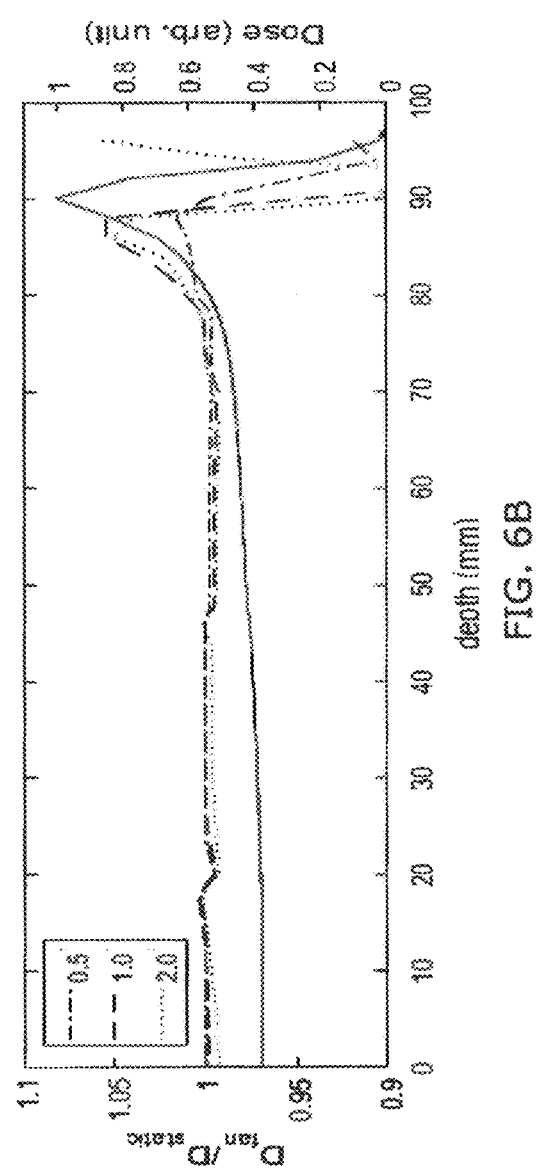
FIG. 6B is a graph of the depth dose along the central axis of an irradiation spot for a static gantry in accordance with aspects of the invention.

The continuous gantry rotation will also affect the dose deposited at each irradiation spot of the treatment plan. As compared to an irradiation spot delivered by a static gantry, the actual delivered proton dose to an irradiation spot during continuous rotation of the gantry will be smeared out to describe a fan. For a given fan angle, the fanning effect of an irradiation spot will depend on the distance from the axis of rotation to the irradiation spot as well as the range of the irradiation spot. The fanning effect impact of gantry rotation on a single irradiation spot can be estimated by taking the ratio of the central axis depth dose of the fan irradiation spot versus a static irradiation spot, centered in the fan (e.g., as seen in FIGS. 6A and 6B). From a purely geometrical standpoint, the fanning effect is larger at the entrance of the spot with the Bragg peak in the isocenter for the on-axis spot. The fanning effect is larger at the Bragg peak for the off-axis spot. From this calculation, it may be estimated that a fan angle of less than 0.5 degree is acceptable within the static irradiation spot approach, both for central as well as off axis irradiation spot positions.

Figure 7:
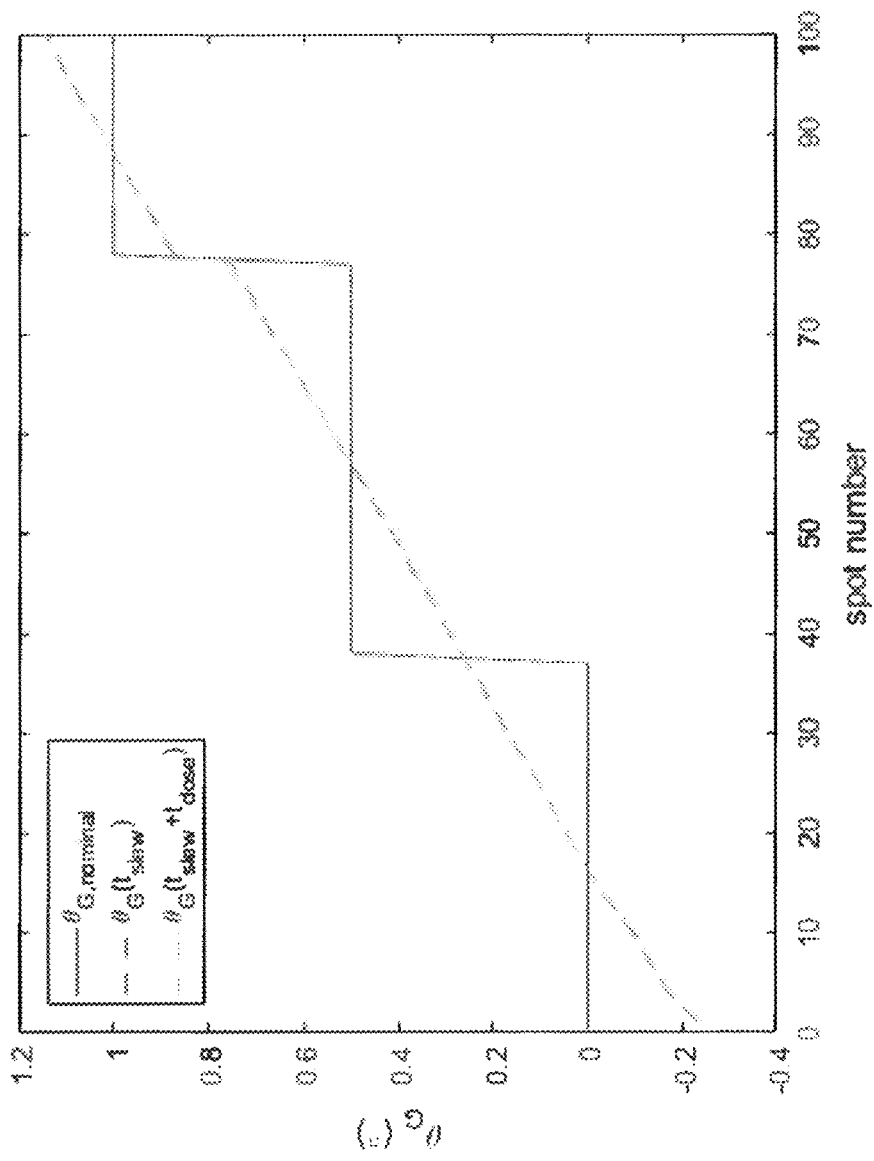
FIG. 7 is a graph illustrating an irradiation plan having groups of irradiation spots where irradiation spots were assigned to groups having a 0.5° difference in gantry angle as compared to an irradiation plan that accounts for the gantry angle during the delivery of protons to each irradiation point in accordance with aspects of the invention.
Figure 8:
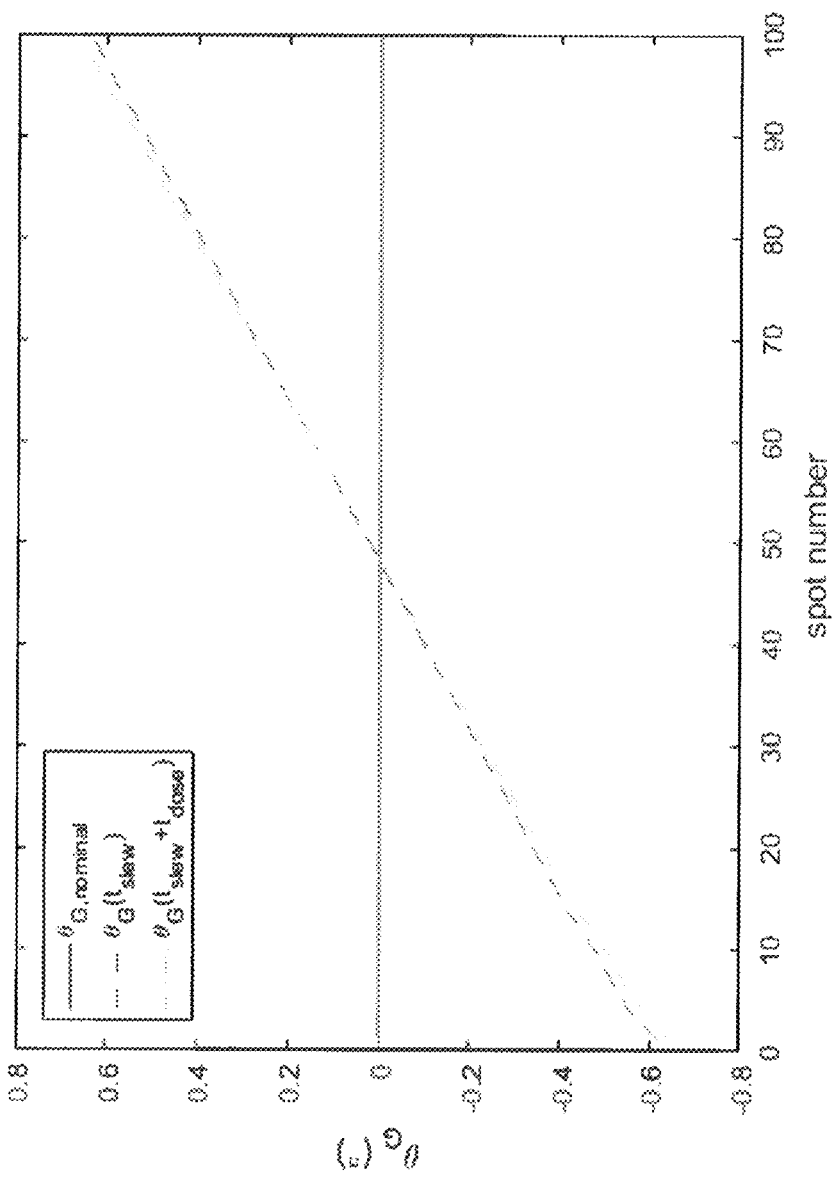
FIG. 8 is a graph illustrating an irradiation plan, where the all the irradiation spots were associated with a single gantry angle as compared to an irradiation plan that accounts for the gantry angle during the delivery of protons to each irradiation point according to aspects of the invention.

FIG. 7 is a graph illustrating an irradiation plan having groups of irradiation spots where irradiation spots were assigned to groups having a 0.5° difference in gantry angle. FIG. 8 is a graph illustrating an irradiation plan, where all the irradiation spots were assigned to a single group associated with a single gantry angle (e.g., an irradiation plan that delivers a proton dosage to each irritation spot using a static gantry). The solid lines in FIGS. 6 and 7 indicate the gantry angle associated with the group(s) of irradiation spots. The dashed line shows the actual angle of a gantry that continuously rotates with respect to the target, taking into account the slew time. The dash-dotted line is the actual angle of a gantry that continuously rotates with respect to the target, taking into account both slew and spot time. The gantry angles of the spots for the dashed line and the dash-dotted line are centered around the nominal gantry angle of each control point or irradiation plan.

EXAMPLES

The following examples are for illustrative purposes and should not be understood as limiting the disclosure. PMAT plans were created for three different cases, consisting of a lung phantom case, a CNS case, and a prostate case. For all cases, the PMAT plan based on a static irradiation plans of four-degree separation was compared with the corresponding PMAT irradiation plan based on the grouping of irradiation spots as described above, using the full modelling of the rotation and using an individual gantry angle per spot. The irradiation plans having groups of irradiation spots was produced by an iterative process discussed above and represented in FIG. 9A-B.

In order to verify that the assignment of more than one irradiation spot to a group is sufficient to model the gantry rotation, the optimized irradiation plans were recalculated, using the slew time and beam current to calculate the actual gantry angle for each spot. The gantry angles of the individual spots ($\Delta\theta_{G,i}$) are centered around the original gantry angle, i.e. for a given control point i, with ni spots positioned at the nominal gantry angle ($\Delta\theta_{G,nom,i}$) the gantry will in total rotate the angle interval.

$$\Delta\theta_{G,i} = \frac{d\theta_i}{dt}\left[\sum_{j=1}^{n_i} t_{slew,j} + t_{spot,j}\right] \quad (1)$$

Each spot j within the control point i may then be assigned its own gantry angle.

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

The spot time was calculated using the beam current, which in turn was estimated using the timings from the beam delivery logs versus the corresponding MU. The number of protons per MU was extracted from Monte Carlo beam data for the treatment unit in question. The beam current was estimated to 4 nA using this data. The plan containing the fully modelled gantry rotation will now have one irradiation spot per control point or irradiation plan (see FIGS. 7 and 8). The spot weights achieved in the optimization using the static (i.e. all irradiation points calculated at the same gantry angle) and the group of irradiation spots were used to calculate a more accurate representation of the actual dose delivered. The accuracy of the two levels of modelling of the rotation (one gantry angle for all the irradiation spots or groups of irradiation spots associated with a respective gantry angle based on the slew time) can be evaluated versus the full modelling of the gantry rotation. The gamma distribution was used to evaluate the differences in proton dose versus the modelling of the full rotation. The criterion for the gamma function was set at 1%/1 mm, and only voxels with a dose D>0.01 Dmax were considered. In order to evaluate the effect of splitting the control points without redoing the raytracing, the target coverage of the plan using the static control points and the split control points have been evaluated using the homogeneity index and the conformity index.

For all three test cases, the target volume, the proton dose per fraction and the corresponding slew and spot time were determined (See Table 1, below). The results show that the slew time increases with increasing target volume. The spot time is negligible compared to the slew time. Arc energies and number of control points and/or irradiation plans after the assigning of irradiation spots to groups is also listed in Table 1. The total number of groups of irradiation points increases with increasing target volume.

TABLE 1

| Plan | Target volume (cm³) | Dose per fraction (Gy) | Arc energy (MeV) | $t_{slew}$ (s) | $t_{spot}$ (s) | No. of control points after split |
|---|---|---|---|---|---|---|
| Lung phantom | 39.2 | 1.3 | 108.4 | 7.74 | 0.27 | 150 |
|  |  |  | 120.3 | 7.51 | 0.29 | 140 |
| Prostate | 65.3 | 1.9 | 130.2 | 11.98 | 0.95 | 177 |
|  |  |  | 161.3 | 9.25 | 1.99 | 144 |
| CNS | 245.0 | 1.7 | 98.4 | 29.7 | 1.65 | 399 |
|  |  |  | 108.4 | 26.6 | 1.64 | 367 |

Table 1 provides the total slew time and spot time for the plans included in this study. The initial number of groups of irradiation spots for all plans was 90.

Figure 10A:
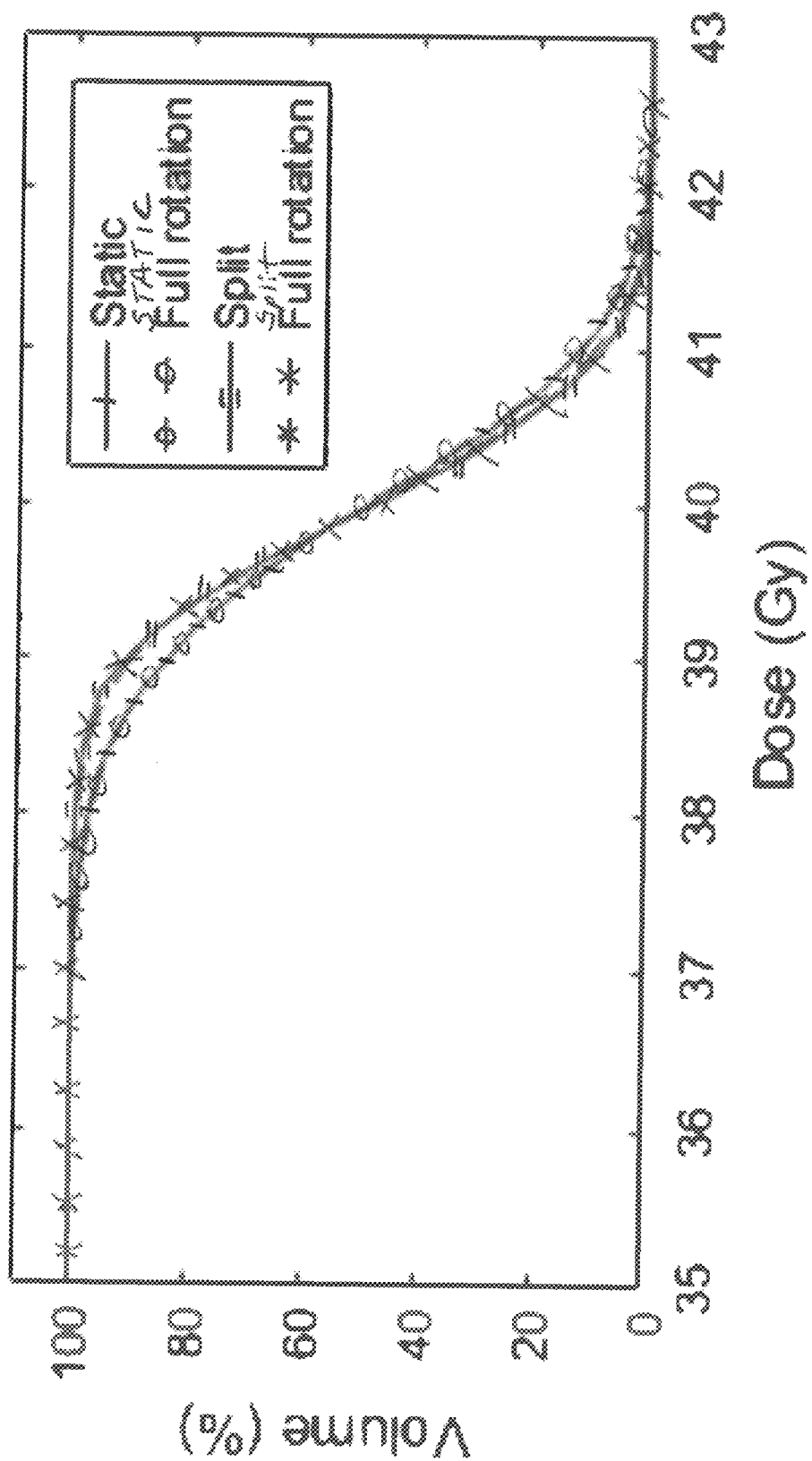
FIG. 10A is a graph of the proton dose delivered to a target of the lung phantom in accordance with the present disclosure.
Figure 10B:
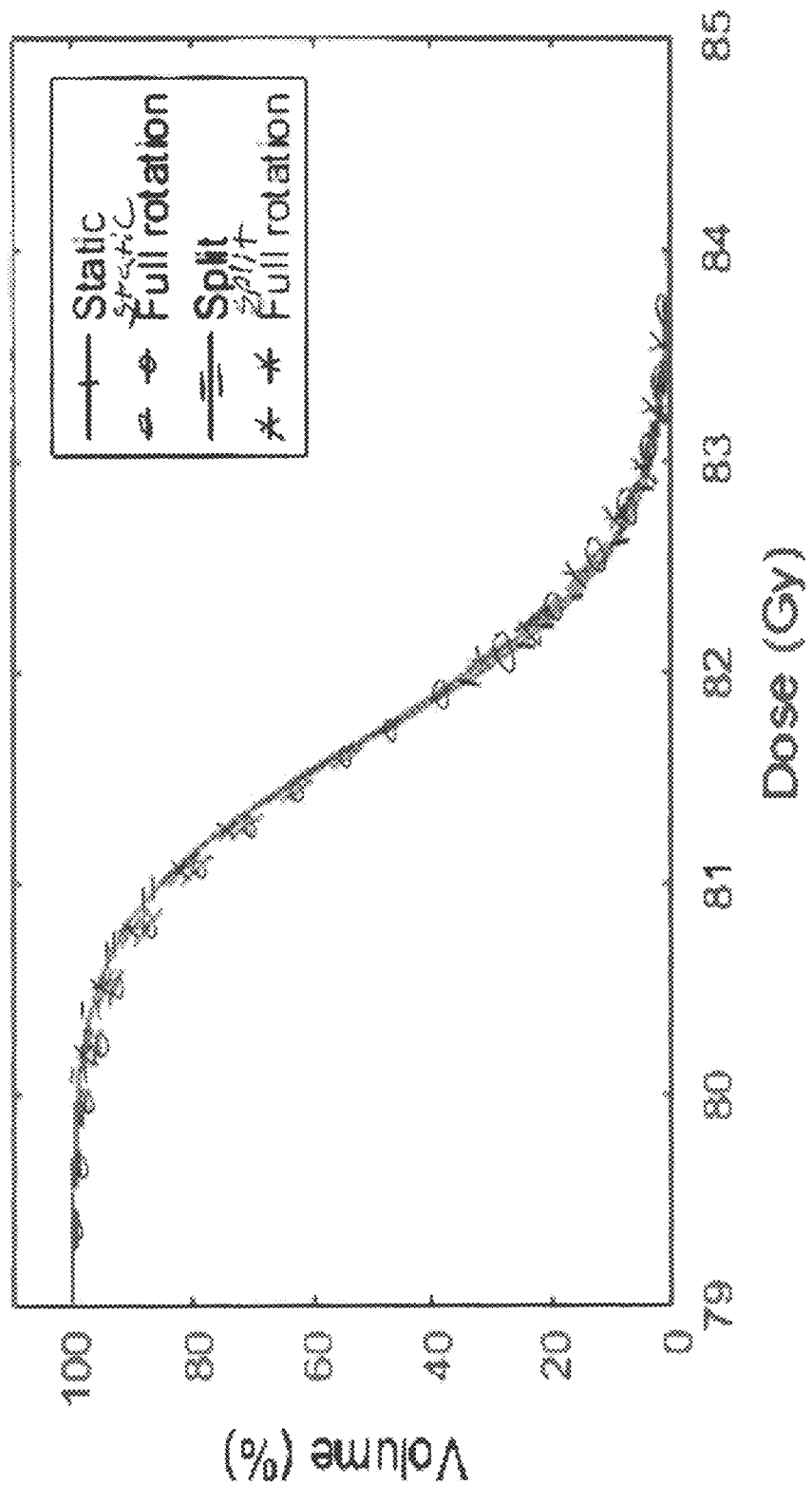
FIG. 10B is a graph of the proton dose delivered to the target of the prostate case in accordance with the present disclosure.
Figure 10C:
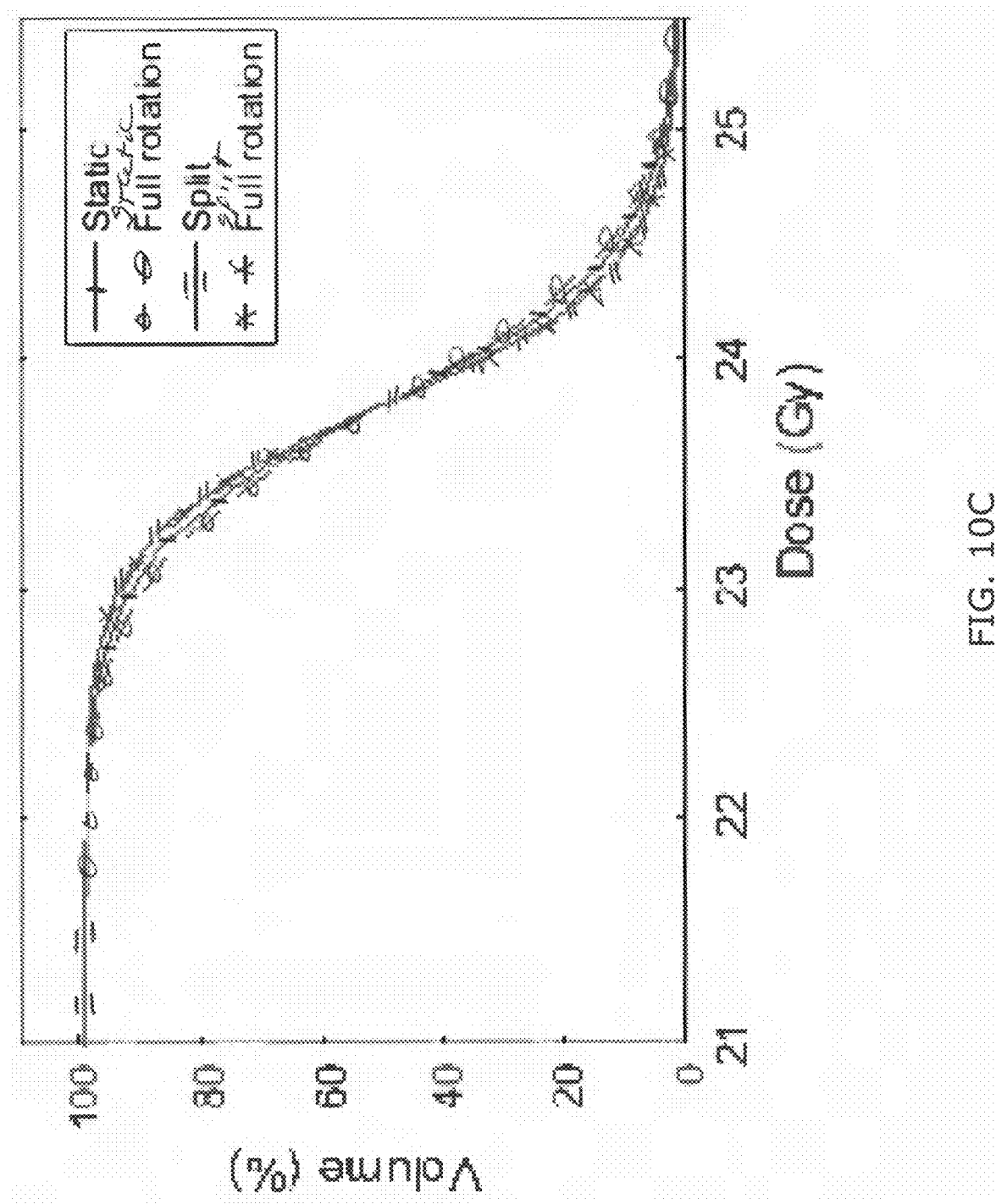
FIG. 10C is a graph of the proton dose delivered to the target of the CNS case in accordance with the present disclosure.

The plans in this study have been optimized for target coverage. FIGS. 10A-10C are graphs of the lung phantom case, prostate case, and CNS, case respectively. The irradiation spots are to be delivered over a 4° change in gantry angle presuming the gantry continuously rotates at a consistent speed with respect to the target during the delivery of the proton dosage to the irradiation spots. In FIGS. 10A-10C, the "Static"/"Static Full Rotation" lines represent irradiation plans having all the irradiation spots calculated based on the same gantry angle (also referred herein as a "static" plan because calculation utilizes the same gantry angle for each of the irradiation spots). The "Split"/"Split Full Rotation" lines in FIGS. 10A-10C represent irradiation plans having a plurality of groups of irradiation spots, where each group of irradiation spots is associated with a respective gantry angle. The groups of irradiation spots only included irradiation spots within a 0.5° change in gantry angle. The term "Full Rotation" as used herein and in FIGS. 10A-10C represents irradiation plans were the actual angle of the gantry at the delivery of the protons to the irradiation spot is used.

Additionally and/or alternatively, the smaller the target volume, the smaller the difference observed in the dose volume histogram (hereafter "DVH") of the static plan versus the full rotation plan as well as the split versus the full rotation plan. Moving to larger volumes, the difference between the static control points and the full rotation is larger, decreasing the dose uniformity in the target. For all three cases, the difference in target DVH is smaller for the split control point approach compared to the full rotation.

In order to evaluate the effect of assigning and reassigning irradiation spots to a plurality of groups and associating a gantry angle with a respective group of irradiation spots without redoing the raytracing, we have calculated the homogeneity and conformity index for all three cases. Table 2, provided below, shows that the full simulation of the rotation displays a small increase in homogeneity index when simulating the full rotation for both static plans and plans having groups of irradiation spots, i.e. the homogeneity is slightly overestimated in both plans with respect to the full rotation simulation. No significant trend of the homogeneity or conformity indices can be seen comparing the static plan versus the irradiation plan having a group of irradiation spots.

TABLE 2

| Plan | $HI_{plan}$ | $HI_{rot}$ | $CI_{plan}$ | $CI_{rot}$ |
| --- | --- | --- | --- | --- |
| Lung phantom static layers | 7.77 | 7.94 | 0.92 | 0.92 |
| Lung phantom, split layers | 6.01 | 6.41 | 0.95 | 0.94 |
| CNS, static layers | 8.80 | 9.52 | 0.85 | 0.85 |
| CNS split layers | 7.83 | 8.05 | 0.84 | 0.84 |
| Prostate, static layers | 2.81 | 3.25 | 0.46 | 0.46 |
| Prostate split ayers | 2.89 | 3.04 | 0.46 | 0.46 |

Figure 11A:
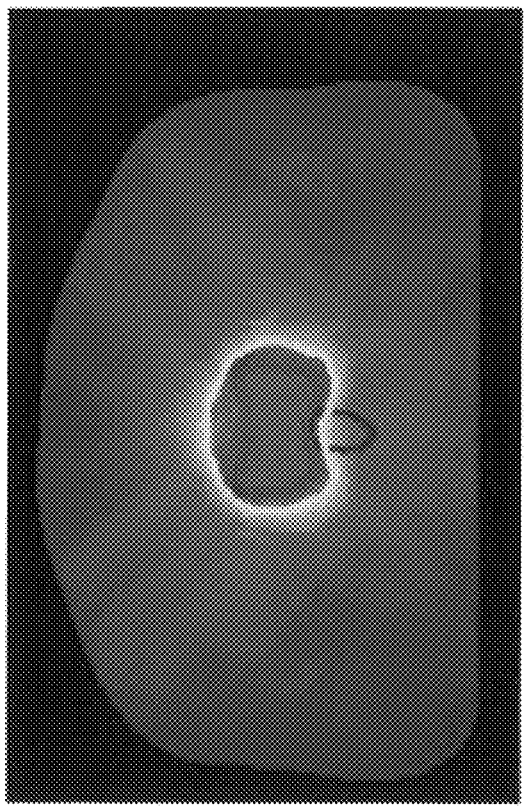
FIG. 11A are images of the dose distribution in the isocenter plane for the static irradiation plans and the irradiation plans having groups of irradiation spots for the prostate case according to aspects of the invention.
Figure 11A:
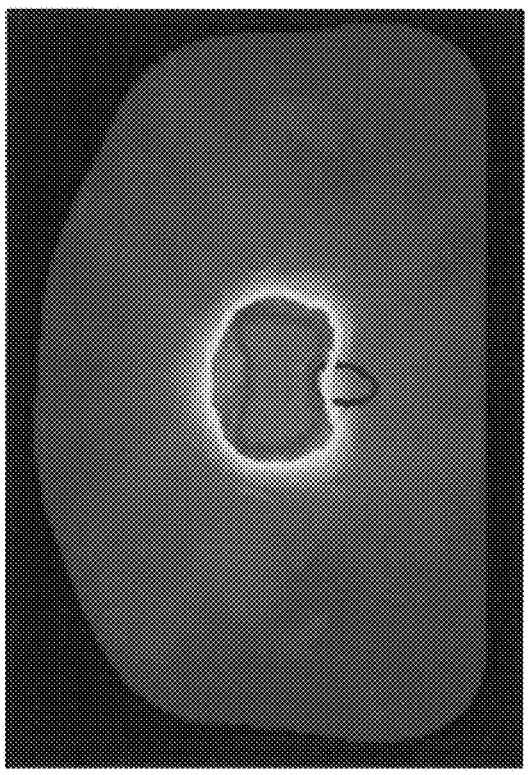
Figure 11B:
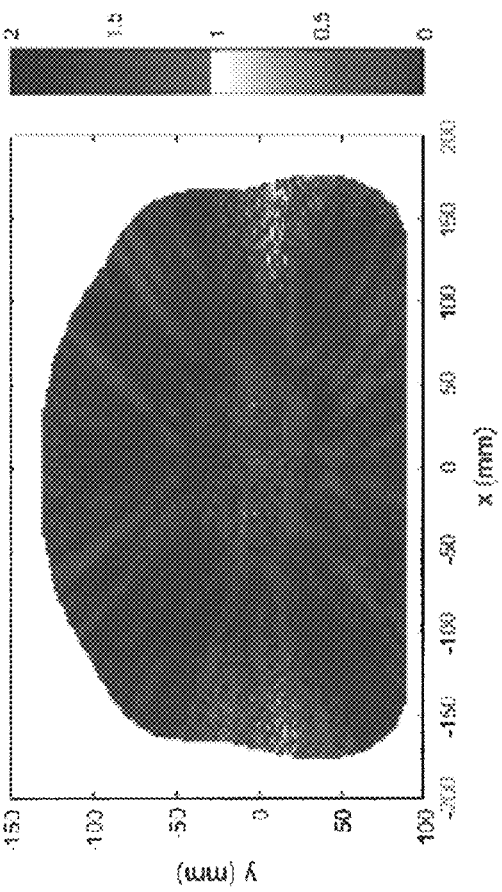
FIG. 11B are images of the gamma distribution in the isocenter plane for the static irradiation plans and the irradiation plans having groups of irradiation spots for the prostate case in accordance with aspects of the invention.
Figure 11B:
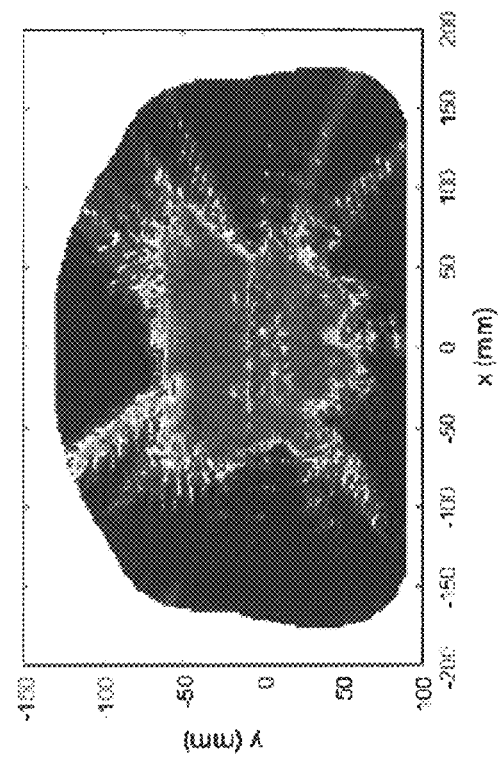
Figure 12A:
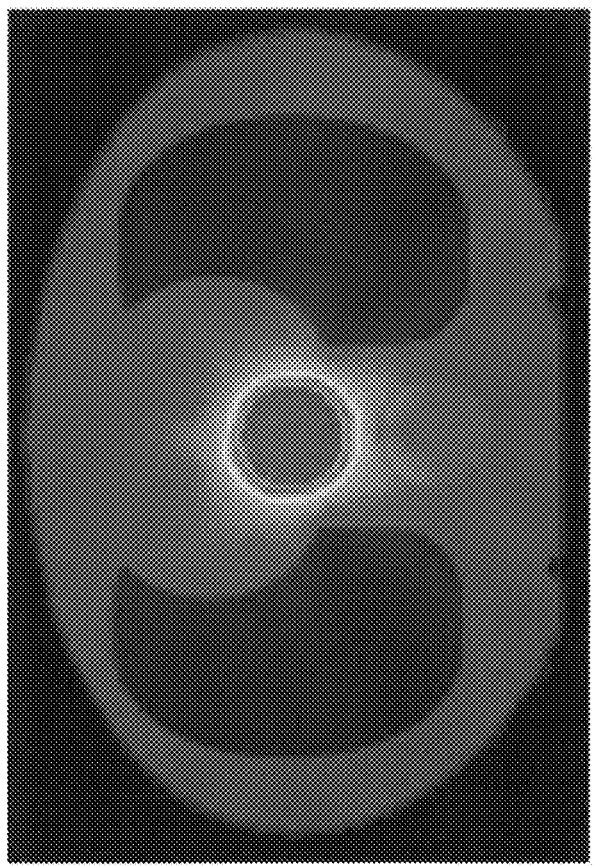
FIG. 12A are images of the dose distribution in the isocenter plane for the static irradiation plans and the irradiation plans having groups of irradiation spots for the lung phantom according to aspects of the invention.
Figure 12A:
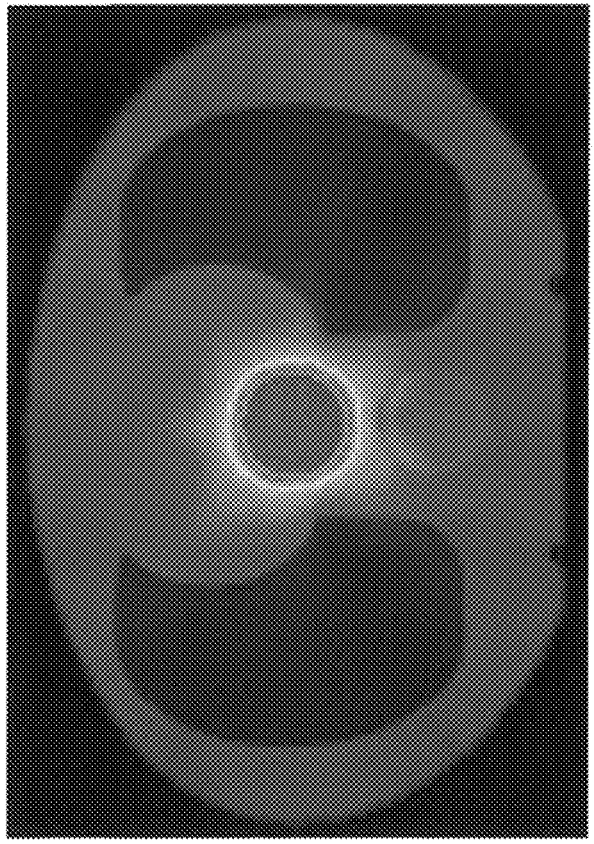
Figure 12B:
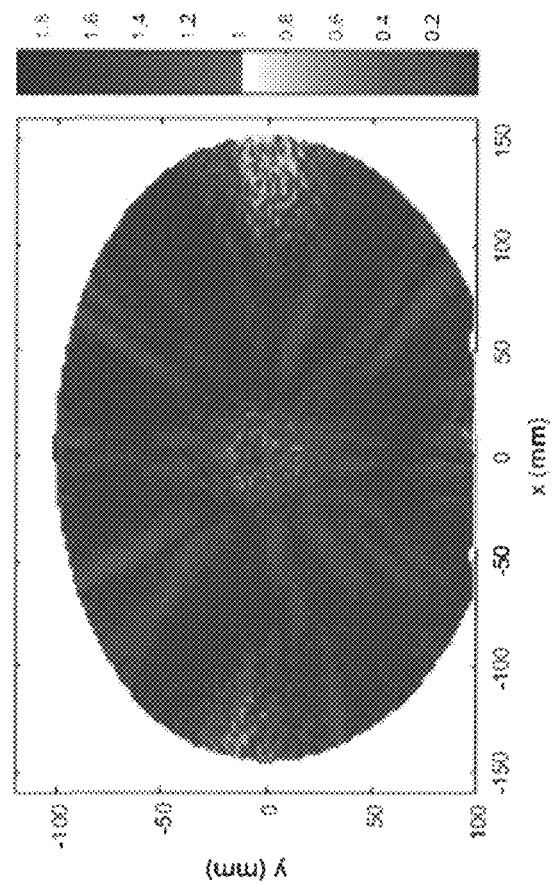
FIG. 12B are images of the gamma distribution in the isocenter plane for the static irradiation plans and the irradiation plans having groups of irradiation spots for the lung phantom in accordance with aspects of the invention.
Figure 12B:
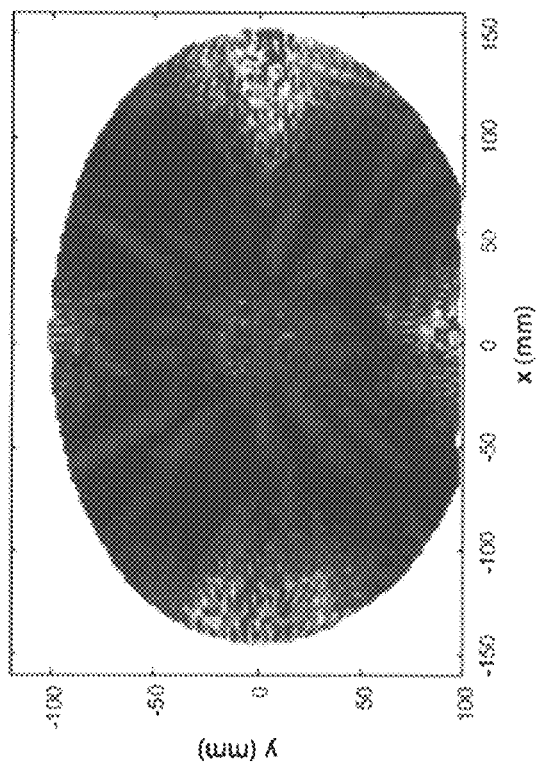
Figure 13A:
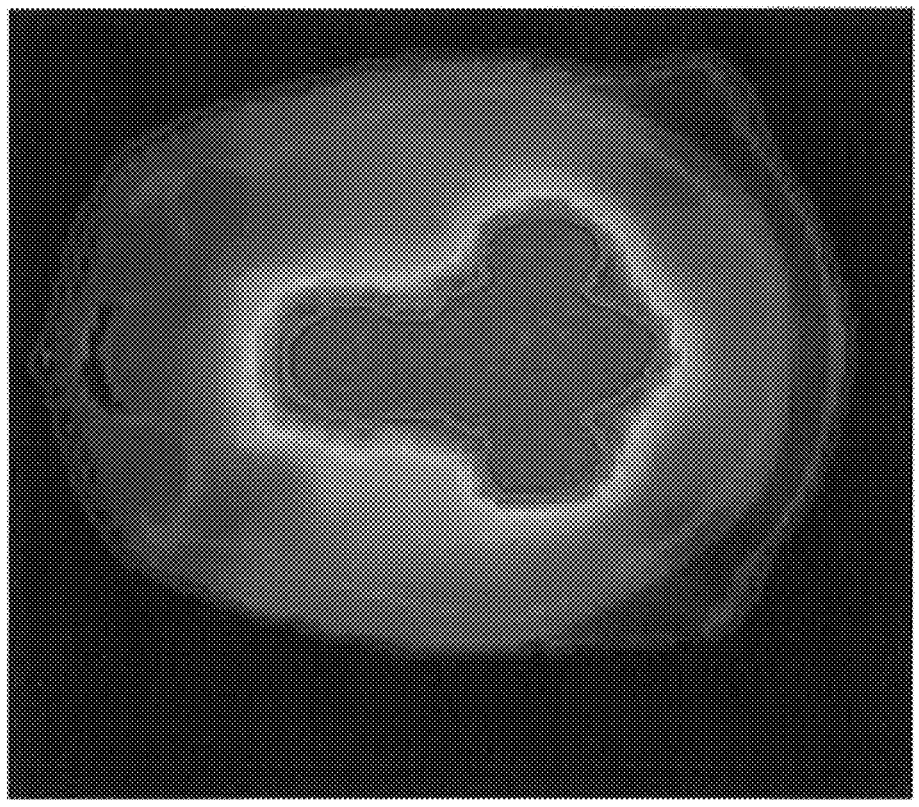
FIG. 13A are images of the dose distribution in the isocenter plane for the static irradiation plans and the irradiation plans having groups of irradiation spots for the CNS case according to aspects of the invention.
Figure 13A:
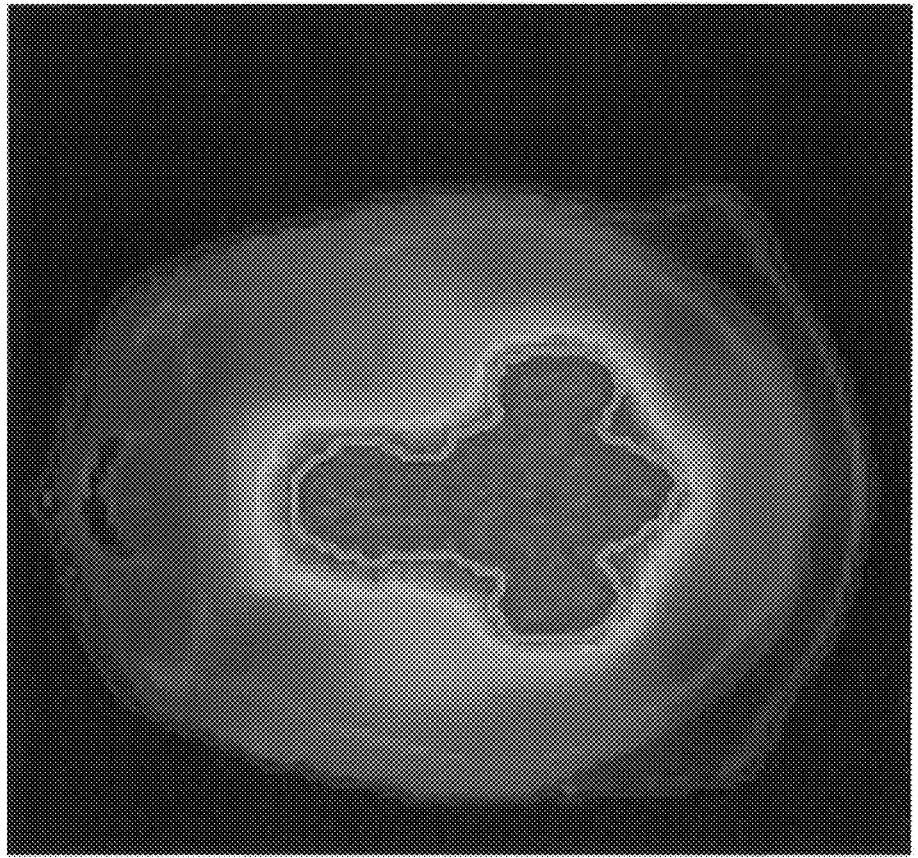
Figure 13B:
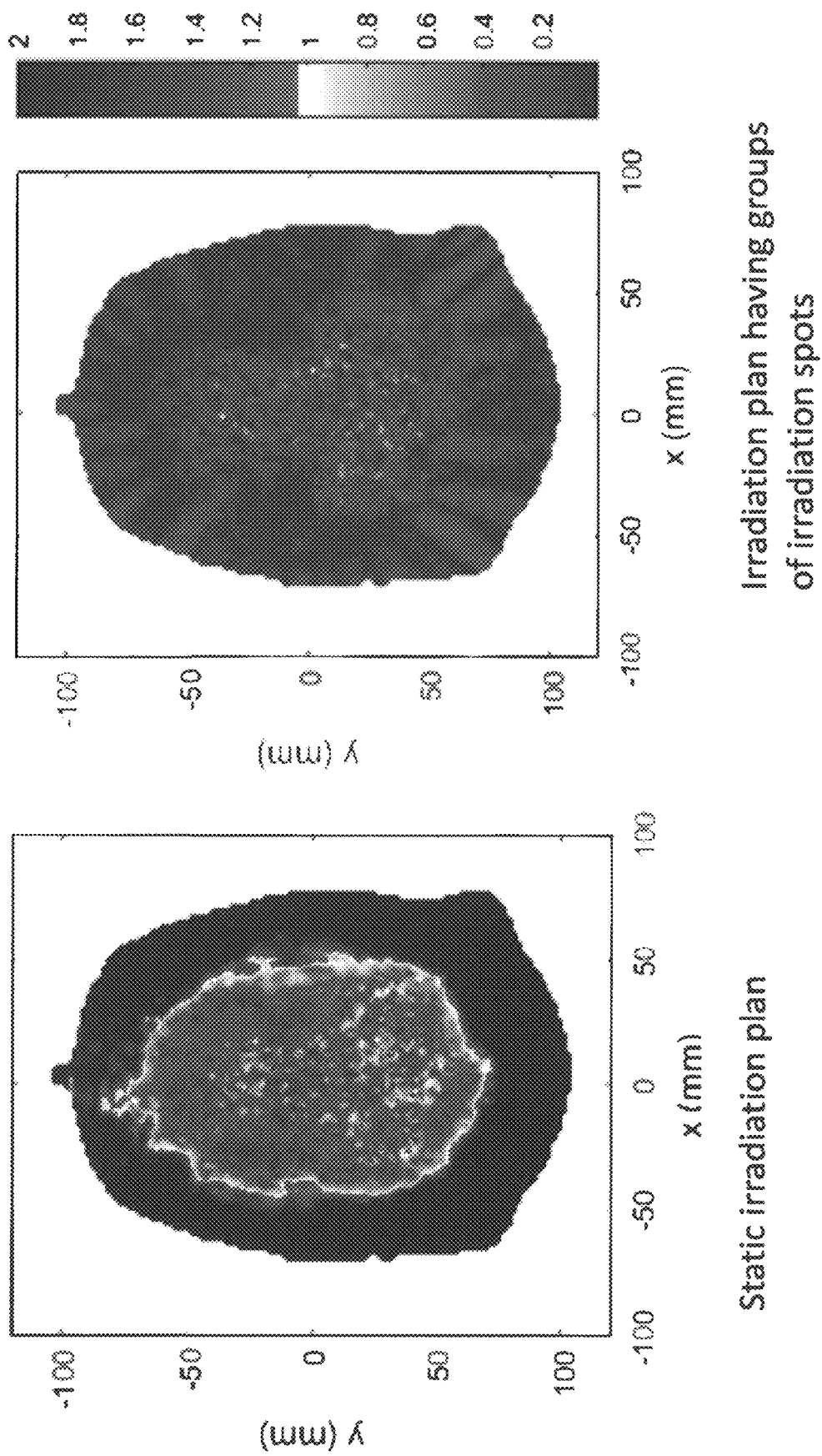
FIG. 13B are images of the gamma distribution in the isocenter plane for the static irradiation plans and the irradiation plans having groups of irradiation spots for the CNS case in accordance with aspects of the invention.

The dose and gamma distribution in the isocenter plane for both the static irradiation plans and the irradiation plans having groups of irradiation spots were compared to the full rotational irradiation plan for the prostate case (see FIGS. 11A and 11B) for the lunch phantom case (see FIGS. 12A and 12B), and for the CNS case (see FIGS. 13A and 13B). The gamma evaluation at 1%/1 mm for the full volume is summarized in Table 3, below.

TABLE 3

| Plan | Static layers vs full rot Voxels passing gamma 1%/1 mm (%) | Split layers vs full rot Voxels passing gamma 1%/1 mm (%) |
| --- | --- | --- |
| Lung phantom | 98.1 | 99.7 |
| CNS | 45.7 | 98.1 |
| Prostate | 19.9 | 99.6 |

From the results presented in Tables 2 and 3, it is clear that the irradiation plans employing groups of irradiation spots, where each group is associated with a respective angular rotation of the gantry is superior to irradiation plans that use single gantry angle for all of the irradiation spots for modeling the delivery of protons to a target when the gantry is continuously rotating with respect to the target. The deviation in target DVH and the accuracy of the dose in the surrounding normal tissue is far better represented when employing an irradiation plan using groups of irradiation spots, as discussed above than irradiation plans that use single gantry angle for all of the irradiation spots.

The methods and systems disclosed herein may be described according to the following aspects.

Aspect 1. A method for creating an irradiation plan, the method comprising, consisting of, or consisting essentially of: receiving an irradiation therapy plan from a computer plan for irradiating a target with a proton beam from a gantry, the irradiation therapy plan including a plurality of irradiation spots for delivering protons to the target; determining a rotational profile for angular rotation of the gantry with respect to the target, a slew time for a proton beam to travel between each of the plurality of irradiation spots, and an amount of protons to be delivered to each irradiation spot; and generating an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

Aspect 2. The method of aspect 1, wherein an angle associated with each of the respective portions of the angular rotation from where the proton beams are to be delivered is determined using the following equations:

$$\Delta\theta_{G,i} = \frac{d\theta_i}{dt}\left[\sum_{j=1}^{n_i} t_{slew,j} + t_{spot,j}\right] \quad (1)$$

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

wherein i represents a number of treatment plans, n is a number of irradiation spots, $\theta_{G,nom,i}$ is the nominal gantry angle, $t_{slew}$ is the slew time associated the time for a proton beam to travel between each of the plurality of irradiation spots, and $t_{spot}$ is the time for delivering a dose of irradiation.

Aspect 3. The method of any one of aspects 1-2, further comprising comparing the amount of protons to be delivered at the plurality of irradiation spots to a threshold value.

Aspect 4. The method of aspect 3, further comprising increasing a number of proton beams if the amount of protons to be delivered to one or more irradiation spots satisfies a threshold value.

Aspect 5. The method of aspect 4, wherein the threshold value is a gamma difference in dose of more than 10 mm/10%.

Aspect 6. The method of aspect 5, wherein the threshold value is a gamma difference in dose of more than 3 mm/3%.

Aspect 7. The method of aspect 6, wherein the threshold value is a gamma difference in dose of more than 1 mm/1%.

Aspect 8. The method of any one of aspects 1-7, wherein the rotational profile of the gantry with respect to the target is a constant 1 rpm.

Aspect 9. The method of aspect 8, wherein the rotational profile of the gantry is 0.5° or less for each treatment plan.

Aspect 10. The method of any one of aspects 1-9, further comprising delivering, based on the irradiation plan, a proton beam to one or more the plurality of irradiation spots of the target.

Aspect 11. A device comprising, consisting of, or consisting essentially of: one or more processors; and memory storing instructions that, when executed by the one or more processors, cause the device to: receive an irradiation therapy plan from a computer plan for irradiating a target with a proton beam from a gantry, the irradiation therapy plan including a plurality of irradiation spots for delivering protons to the target; determine a rotational profile for angular rotation of the gantry with respect to the target, a slew time for a proton beam to travel between each of the plurality of irradiation spots, and an amount of protons to be delivered to each irradiation spot; and generate an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

Aspect 12. The device of aspect 11, wherein an angle associated with each of the respective portions of the angular rotation from where the proton beams are to be delivered is caused to be determined, by the instructions, using the following equations:

$$\Delta\theta_{G,i} = \frac{d\theta_i}{dt}\left[\sum_{j=1}^{n_i} t_{slew,j} + t_{spot,j}\right] \quad (1)$$

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

wherein i represents a number of treatment plans, n is a number of irradiation spots, $\theta_{G,nom,i}$ is the nominal gantry angle, $t_{slew}$ is the slew time associated the time for a proton beam to travel between each of the plurality of irradiation spots, and $t_{spot}$ is the time for delivering a dose of irradiation.

Aspect 13. The device of any one of aspects 11-12, wherein the instructions, when executed by the one or more processors, further cause the device to compare the amount of protons to be delivered at the plurality of irradiation spots to a threshold value.

Aspect 14. The device of aspect 13, wherein the instructions, when executed by the one or more processors, further cause the device to increase a number of proton beams if the amount of protons to be delivered to one or more irradiation spots satisfies a threshold value.

Aspect 15. The device of aspect 14, wherein the threshold value is a gamma difference in dose of more than one or more of 10 mm/10%, 3 mm/3%, or 1 mm/1%.

Aspect 16. The device of any one of aspect 11-15, wherein the rotational profile of the gantry with respect to the target is a constant 1 rpm.

Aspect 17. The device of aspect 16, wherein the rotational profile of the gantry is 0.5° or less for each treatment plan.

Aspect 18. The device of any one of aspects 11-17, wherein the instructions, when executed by the one or more processors, further cause the device to deliver, based on the irradiation plan, a proton beam to one or more the plurality of irradiation spots of the target.

Aspect 19. A non-transitory computer-readable medium comprising computer-executable instructions that, when executed by one or more processors, perform the method comprising, consisting of, or consisting essentially of: receiving an irradiation therapy plan from a computer plan for irradiating a target with a proton beam from a gantry, the irradiation therapy plan including a plurality of irradiation spots for delivering protons to the target; determining a rotational profile for angular rotation of the gantry with respect to the target, a slew time for a proton beam to travel between each of the plurality of irradiation spots, and an amount of protons to be delivered to each irradiation spot; and generating an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

Aspect 20. The computer-readable medium of aspect 19, wherein the instructions, when executed by the one or more processors, further perform delivering, based on the irradiation plan, a proton beam to one or more the plurality of irradiation spots of the target.

Aspect 21. A non-transitory computer-readable medium storing instructions that, when executed by one or more processors, cause a device to perform the methods of any one of aspects 1-10.

Figure 14:
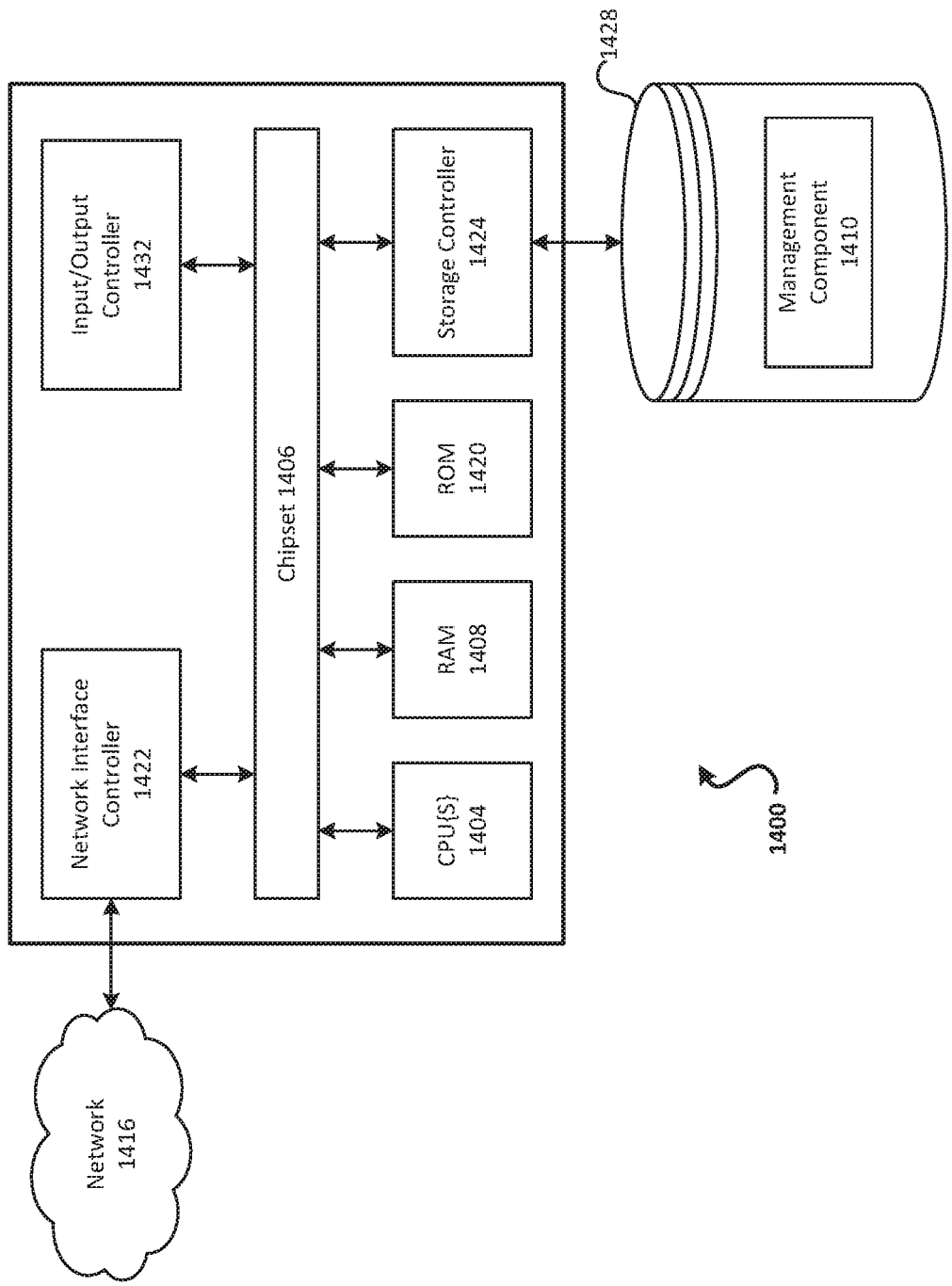
FIG. 14 depicts a computing device that may be used to implement the methods and systems described herein.

FIG. 14 depicts a computing device that may be used in various aspects, such as the devices described herein. For example, the proton therapy plan generator 110, the proton delivery system 120, the controller 122, the gantry 124, and the patient positioning device 126 may each be implemented in an instance of a computing device 1400 of FIG. 14. The computer architecture shown in FIG. 14 shows a conventional server computer, workstation, desktop computer, laptop, tablet, network appliance, PDA, e-reader, digital cellular phone, or other computing node, and may be utilized to execute any aspects of the computers described herein, such as to implement the methods described herein (e.g., as shown FIG. 3 and FIG. 9A-B and described elsewhere).

The computing device 1400 may include a baseboard, or "motherboard," which is a printed circuit board to which a multitude of components or devices may be connected by way of a system bus or other electrical communication paths. One or more central processing units (CPUs) 1404 may operate in conjunction with a chipset 1406. The CPU(s) 1404 may be standard programmable processors that perform arithmetic and logical operations necessary for the operation of the computing device 1400.

The CPU(s) 1404 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

The CPU(s) 1404 may be augmented with or replaced by other processing units, such as GPU(s) 1405. The GPU(s) 1405 may comprise processing units specialized for but not necessarily limited to highly parallel computations, such as graphics and other visualization-related processing.

A chipset 1406 may provide an interface between the CPU(s) 1404 and the remainder of the components and devices on the baseboard. The chipset 1406 may provide an interface to a random access memory (RAM) 1408 used as the main memory in the computing device 1400. The chipset 1406 may further provide an interface to a computer-readable storage medium, such as a read-only memory (ROM) 1420 or non-volatile RAM (NVRAM) (not shown), for storing basic routines that may help to start up the computing device 1400 and to transfer information between the various components and devices. ROM 1420 or NVRAM may also store other software components necessary for the operation of the computing device 1400 in accordance with the aspects described herein.

The computing device 1400 may operate in a networked environment using logical connections to remote computing nodes and computer systems through local area network (LAN) 1416. The chipset 1406 may include functionality for providing network connectivity through a network interface controller (NIC) 1422, such as a gigabit Ethernet adapter. A NIC 1422 may be capable of connecting the computing device 1400 to other computing nodes over a network 1416. It should be appreciated that multiple NICs 1422 may be present in the computing device 1400, connecting the computing device to other types of networks and remote computer systems.

The computing device 1400 may be connected to a mass storage device 1428 that provides non-volatile storage for the computer. The mass storage device 1428 may store system programs, application programs, other program modules, and data, which have been described in greater detail herein. The mass storage device 1428 may be connected to the computing device 1400 through a storage controller 1424 connected to the chipset 1406. The mass storage device 1428 may consist of one or more physical storage units. A storage controller 1424 may interface with the physical storage units through a serial attached SCSI (SAS) interface, a serial advanced technology attachment (SATA) interface, a fiber channel (FC) interface, or other type of interface for physically connecting and transferring data between computers and physical storage units.

The computing device 1400 may store data on a mass storage device 1428 by transforming the physical state of the physical storage units to reflect the information being stored. The specific transformation of a physical state may depend on various factors and on different implementations of this description. Examples of such factors may include, but are not limited to, the technology used to implement the physical storage units and whether the mass storage device 1428 is characterized as primary or secondary storage and the like.

For example, the computing device 1400 may store information to the mass storage device 1428 by issuing instructions through a storage controller 1424 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computing device 1400 may further read information from the mass storage device 1428 by detecting the physical states or characteristics of one or more particular locations within the physical storage units.

In addition to the mass storage device 1428 described above, the computing device 1400 may have access to other computer-readable storage media to store and retrieve information, such as program modules, data structures, or other data. It should be appreciated by those skilled in the art that computer-readable storage media may be any available media that provides for the storage of non-transitory data and that may be accessed by the computing device 1400.

By way of example and not limitation, computer-readable storage media may include volatile and non-volatile, transitory computer-readable storage media and non-transitory computer-readable storage media, and removable and non-removable media implemented in any method or technology. Computer-readable storage media includes, but is not limited to, RAM, ROM, erasable programmable ROM ("EPROM"), electrically erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage, other magnetic storage devices, or any other medium that may be used to store the desired information in a non-transitory fashion.

A mass storage device, such as the mass storage device 1428 depicted in FIG. 14, may store an operating system utilized to control the operation of the computing device 1400. The operating system may comprise a version of the LINUX operating system. The operating system may comprise a version of the WINDOWS SERVER operating system from the MICROSOFT Corporation. According to further aspects, the operating system may comprise a version of the UNIX operating system. Various mobile phone operating systems, such as IOS and ANDROID, may also be utilized. It should be appreciated that other operating systems may also be utilized. The mass storage device 1428 may store other system or application programs and data utilized by the computing device 1400.

Figure 9A:
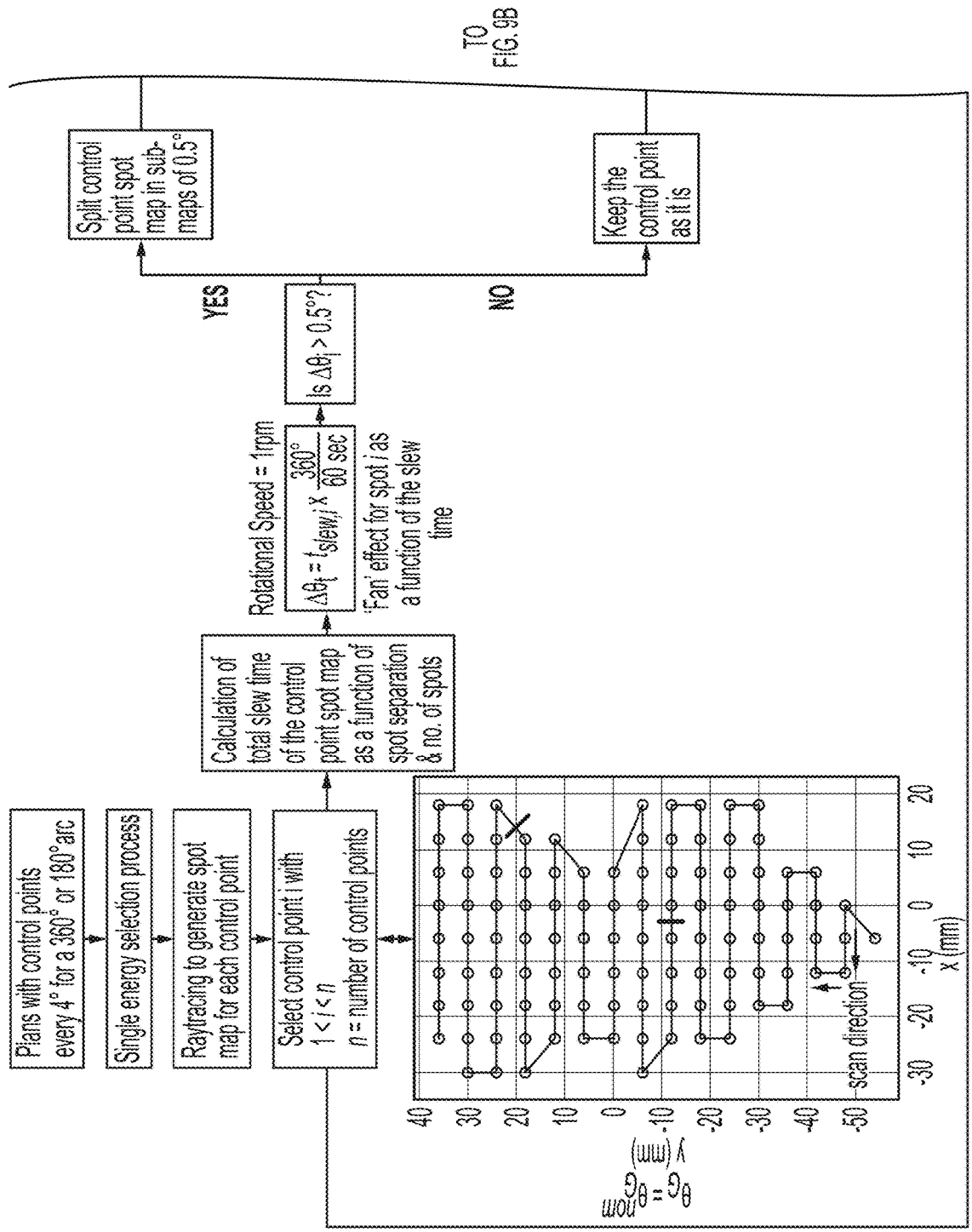
FIGS. 9A and 9B show a non-limiting exemplary flow chart of the method of FIG. 2 for producing an irradiation plan having a plurality of group of irradiation spots.
Figure 9B:
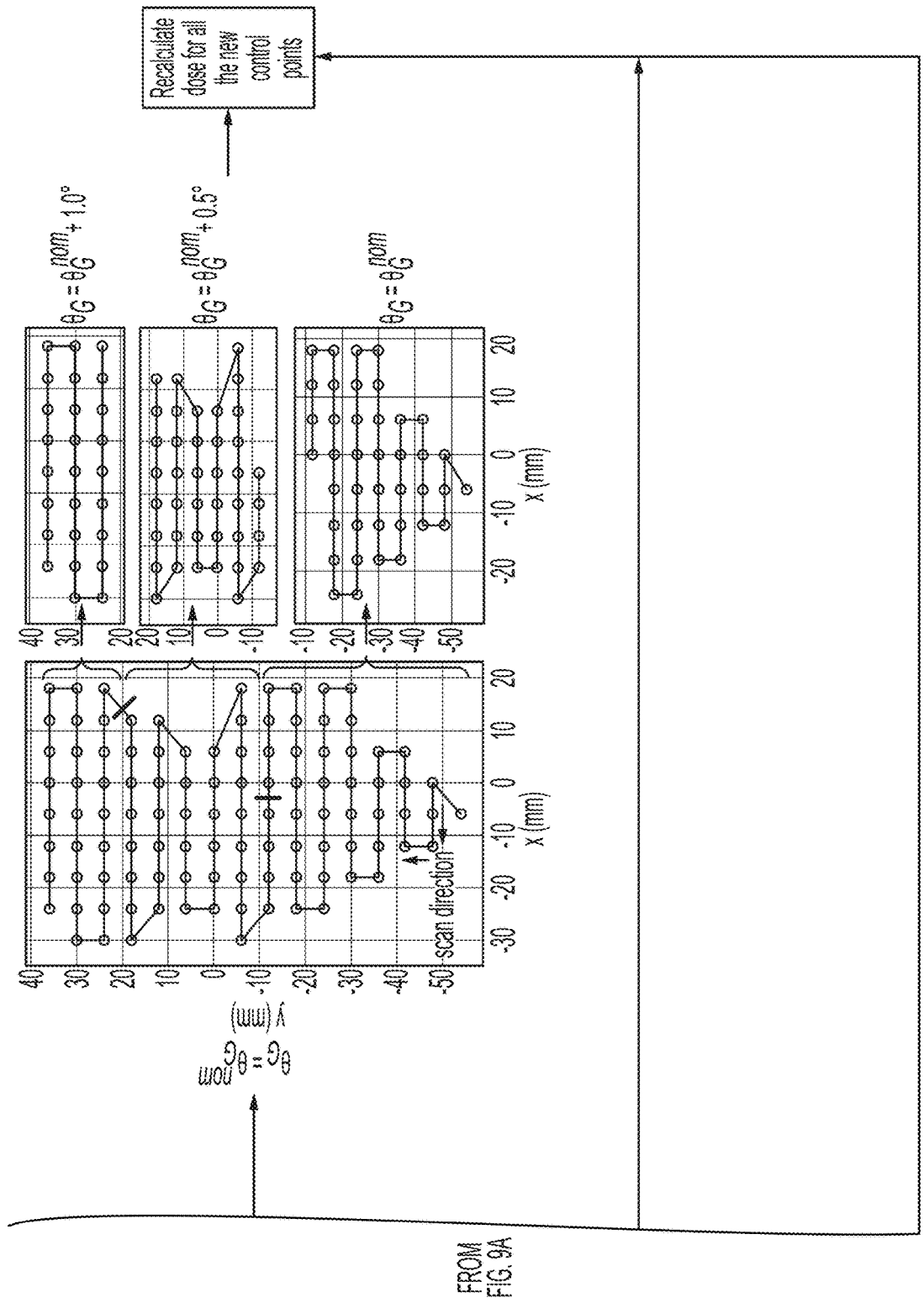

The mass storage device 1428 or other computer-readable storage media may also be encoded with computer-executable instructions, which, when loaded into the computing device 1400, transforms the computing device from a general-purpose computing system into a special-purpose computer capable of implementing the aspects described herein. These computer-executable instructions transform the computing device 1400 by specifying how the CPU(s) 1404 transition between states, as described above. The computing device 1400 may have access to computer-readable storage media storing computer-executable instructions, which, when executed by the computing device 1400, may perform the methods described further herein (e.g., as shown in FIG. 3, FIG. 9A-B and described elsewhere)

A computing device, such as the computing device 1400 depicted in FIG. 14, may also include an input/output controller 1432 for receiving and processing input from a number of input devices, such as a keyboard, a mouse, a touchpad, a touch screen, an electronic stylus, or other type of input device. Similarly, an input/output controller 1432 may provide output to a display, such as a computer monitor, a flat-panel display, a digital projector, a printer, a plotter, or other type of output device. It will be appreciated that the computing device 1400 may not include all of the components shown in FIG. 14, may include other components that are not explicitly shown in FIG. 14, or may utilize an architecture completely different than that shown in FIG. 14.

As described herein, a computing device may be a physical computing device, such as the computing device 1400 of FIG. 14. A computing node may also include a virtual machine host process and one or more virtual machine instances. Computer-executable instructions may be executed by the physical hardware of a computing device indirectly through interpretation and/or execution of instructions stored and executed in the context of a virtual machine.

Although the invention is illustrated and described herein with reference to specific embodiments, the invention is not intended to be limited to the details shown. Rather, various modifications may be made in the details within the scope and range of equivalents of the claims and without departing from the invention.

It is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. The word "includes" and variations of the word, such as "including" and "includes," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Components are described that may be used to perform the described methods and systems. When combinations, subsets, interactions, groups, etc., of these components are described, it is understood that while specific references to each of the various individual and collective combinations and permutations of these may not be explicitly described, each is specifically contemplated and described herein, for all methods and systems. This applies to all aspects of this application including, but not limited to, operations in described methods. Thus, if there are a variety of additional operations that may be performed it is understood that each of these additional operations may be performed with any specific embodiment or combination of embodiments of the described methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, may be implemented by computer program instructions. These computer program instructions may be loaded on a general-purpose computer, special-purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that may direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto may be performed in other sequences that are appropriate. For example, described blocks or states may be performed in an order other than that specifically described, or multiple blocks or states may be combined in a single block or state. The example blocks or states may be performed in serial, in parallel, or in some other manner. Blocks or states may be added to or removed from the described example embodiments. The example systems and components described herein may be configured differently than described. For example, elements may be added to, removed from, or rearranged compared to the described example embodiments.

It will also be appreciated that various items are illustrated as being stored in memory or on storage while being used, and that these items or portions thereof may be transferred between memory and other storage devices for purposes of memory management and data integrity. Alternatively, in other embodiments, some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

While the methods and systems have been described in connection with preferred embodiments and specific examples, it is not intended that the scope be limited to the particular embodiments set forth, as the embodiments herein are intended in all respects to be illustrative rather than restrictive.

It will be apparent to those skilled in the art that various modifications and variations may be made without departing from the scope or spirit of the present disclosure. Other embodiments will be apparent to those skilled in the art from consideration of the specification and practices described herein. It is intended that the specification and example figures be considered as exemplary only, with a true scope and spirit being indicated by the following claims.

What is claimed:

1. A method for creating an irradiation plan, the method comprising:
receiving an irradiation therapy plan from a computer plan for irradiating a target with a proton beam from a gantry, the irradiation therapy plan including a plurality of irradiation spots for delivering protons to the target;
determining a rotational profile for angular rotation of the gantry with respect to the target, a slew time for a proton beam to travel between each of the plurality of irradiation spots, and an amount of protons to be delivered to each irradiation spot; and
generating an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

2. The method of claim 1, wherein an angle associated with each of the respective portions of the angular rotation from where the proton beams are to be delivered is determined using the following equations:

$$\Delta\theta_{G,i} = \frac{d\theta_i}{dt}\left[\sum_{j=1}^{n_i} t_{slew,j} + t_{spot,j}\right] \quad (1)$$

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

wherein i represents a number of treatment plans, n is a number of irradiation spots, $\theta_{G,\,nom,I}$ is the nominal gantry angle, $t_{slew}$ is the slew time associated the time for a proton beam to travel between each of the plurality of irradiation spots, and $t_{spot}$ is the time for delivering a dose of irradiation.

3. The method of claim 1, further comprising comparing the amount of protons to be delivered at the plurality of irradiation spots to a threshold value.

4. The method of claim 3, further comprising increasing a number of proton beams if the amount of protons to be delivered to one or more irradiation spots satisfies a threshold value.

5. The method of claim 4, wherein the threshold value is a gamma difference in dose of more than 10 mm/10%.

6. The method of claim 5, wherein the threshold value is a gamma difference in dose of more than 3 mm/3%.

7. The method of claim 6, wherein the threshold value is a gamma difference in dose of more than 1 mm/1%.

8. The method of claim 1, wherein the rotational profile of the gantry with respect to the target is a constant 1 rpm.

9. The method of claim 8, wherein the rotational profile of the gantry is 0.5° or less for each treatment plan.

10. The method of claim 1, further comprising delivering, based on the irradiation plan, a proton beam to one or more the plurality of irradiation spots of the target.

11. A device comprising:
one or more processors; and
memory storing instructions that, when executed by the one or more processors, cause the device to:
receive an irradiation therapy plan from a computer plan for irradiating a target with a proton beam from a gantry, the irradiation therapy plan including a plurality of irradiation spots for delivering protons to the target;
determine a rotational profile for angular rotation of the gantry with respect to the target, a slew time for a proton beam to travel between each of the plurality of irradiation spots, and an amount of protons to be delivered to each irradiation spot; and
generate an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

12. The device of claim 11, wherein an angle associated with each of the respective portions of the angular rotation from where the proton beams are to be delivered is caused to be determined, by the instructions, using the following equations:

$$\Delta\theta_{G,i} = \frac{d\theta_i}{dt}\left[\sum_{j=1}^{n_i} t_{slew,j} + t_{spot,j}\right] \quad (1)$$

$$\theta_{G,j} = \theta_{G,nom,i} - \frac{\Delta\theta_i}{2} + \frac{d\theta}{dt}\left[\sum_{k=1}^{j} t_{slew,k} + t_{spot,k}\right] \quad (2)$$

wherein i represents a number of treatment plans, n is a number of irradiation spots, $\theta_{G,nom,I}$ is the nominal gantry angle, $t_{slew}$ is the slew time associated the time for a proton beam to travel between each of the plurality of irradiation spots, and $t_{spot}$ is the time for delivering a dose of irradiation.

13. The device of claim 11, wherein the instructions, when executed by the one or more processors, further cause the device to compare the amount of protons to be delivered at the plurality of irradiation spots to a threshold value.

14. The device of claim 13, wherein the instructions, when executed by the one or more processors, further cause the device to increase a number of proton beams if the amount of protons to be delivered to one or more irradiation spots satisfies a threshold value.

15. The device of claim 14, wherein the threshold value is a gamma difference in dose of more than one or more of 10 mm/10%, 3 mm/3%, or 1 mm/1%.

16. The device of claim 11, wherein the rotational profile of the gantry with respect to the target is a constant 1 rpm.

17. The device of claim 16, wherein the rotational profile of the gantry is 0.5° or less for each treatment plan.

18. The device of claim 11, wherein the instructions, when executed by the one or more processors, further cause the device to deliver, based on the irradiation plan, a proton beam to one or more the plurality of irradiation spots of the target.

19. A non-transitory computer-readable medium comprising computer-executable instructions that, when executed by one or more processors, perform the method comprising:
receiving an irradiation therapy plan from a computer plan for irradiating a target with a proton beam from a gantry, the irradiation therapy plan including a plurality of irradiation spots for delivering protons to the target;
determining a rotational profile for angular rotation of the gantry with respect to the target, a slew time for a proton beam to travel between each of the plurality of irradiation spots, and an amount of protons to be delivered to each irradiation spot; and
generating an irradiation plan, the irradiation plan including a plurality of groups of irradiation spots based on the determined rotational profile, the slew time, and the amount of protons to be delivered to each irradiation spot, each group of irradiation spots associated with a respective portion of the angular rotation.

20. The computer-readable medium of claim 19, wherein the instructions, when executed by the one or more processors, further perform delivering, based on the irradiation plan, a proton beam to one or more the plurality of irradiation spots of the target.

21. The method of claim 1, wherein the slew time is a function of a distance between irradiation spots of the plurality of irradiation spots and a speed at which the proton beam is manipulated between the irradiation spots.

22. The method of claim 1, wherein determining the irradiation plan comprises determining, based on the slew time, an angular displacement of the gantry for each irradiation spot of an original spot map of the irradiation therapy plan.

23. The method of claim 1, wherein the rotational profile comprises of a speed of the angular rotation of the gantry indicating a rate at which an angle of the gantry changes from one angle to another angle, and wherein the irradiation plan comprises the speed of the angular rotation.

* * * * *